US012564423B2

(12) United States Patent　　　(10) Patent No.: US 12,564,423 B2
Kapur et al.　　　(45) Date of Patent: Mar. 3, 2026

(54) SYSTEMS AND METHODS FOR ACCESSING A RENAL CAPSULE FOR DIAGNOSTIC AND THERAPEUTIC PURPOSES

(71) Applicant: Tufts Medical Center, Inc., Boston, MA (US)

(72) Inventors: Navin K. Kapur, Boston, MA (US); Richard H. Karas, Franklin, MA (US)

(73) Assignee: Tufts Medical Center, Inc., Boston, MA (US)

( * ) Notice: Subject to any disclaimer, the term of this patent is extended or adjusted under 35 U.S.C. 154(b) by 1021 days.

(21) Appl. No.: 17/595,234

(22) PCT Filed: May 12, 2020

(86) PCT No.: PCT/US2020/032523
§ 371 (c)(1),
(2) Date: Nov. 11, 2021

(87) PCT Pub. No.: WO2020/232023
PCT Pub. Date: Nov. 19, 2020

(65) Prior Publication Data
US 2022/0218393 A1　　Jul. 14, 2022

Related U.S. Application Data

(60) Provisional application No. 62/847,781, filed on May 14, 2019.

(51) Int. Cl.
*A61B 17/34* (2006.01)
*A61B 5/00* (2006.01)
(Continued)

(52) U.S. Cl.
CPC ........ *A61B 17/3423* (2013.01); *A61B 5/6851* (2013.01); *A61B 5/6852* (2013.01);
(Continued)

(58) Field of Classification Search
CPC ................ A61B 5/6851; A61B 5/6852; A61B 2018/00511; A61B 2018/00595;
(Continued)

(56) References Cited

U.S. PATENT DOCUMENTS

| | | |
|---|---|---|
| 6,231,551 B1 | 5/2001 | Barbut |
| 6,241,666 B1 | 6/2001 | Pomeranz et al. |

(Continued)

FOREIGN PATENT DOCUMENTS

| | | |
|---|---|---|
| EP | 2978372 A2 | 2/2016 |
| WO | WO-2014160832 A2 | 10/2014 |
| WO | WO-2020232023 A1 | 11/2020 |

OTHER PUBLICATIONS

Kettenbach et al. (2016). Transjugular Renal Biopsy in high-risk patients [PowerPoint Presentation]. Landesklinikum, St Pölten—Lilienfeld. https://s3.eu-central-1.amazonaws.com/meta-dcr/160910_6034_CIRSE_CIRSE_2016_Barcelona/download/download_24351_un.pdf (Year: 2016).*

(Continued)

*Primary Examiner* — Charles A Marmor, II
*Assistant Examiner* — Andrew E Hoffpauir
(74) *Attorney, Agent, or Firm* — Greenberg Traurig, LLP; Christopher C. Bolten; Albert K. Heng

(57) ABSTRACT

Systems and methods are provided for accessing a renal capsule of a patient's kidney in a minimally invasive manner for therapeutic and/or diagnostic purposes. The method includes advancing the distal end of a catheter into the subcapsular space of the renal capsule and performing the therapeutic and/or diagnostic procedure(s). With access to the renal capsule, the catheter may be used to, for example, remove fluid from the subcapular space, decapsulate the renal capsule by disrupting the fibrous capsule of the renal capsule to relieve renal pressure, displace the fibrous capsule (Continued)

100 from the kidney, measure/monitor renal pressure within the kidney, and/or deliver drug therapy and/or stem cells, viruses for gene therapy, RNAi, nanoparticles, dyes, etc. to the subcapsular space of the renal capsule.

32 Claims, 24 Drawing Sheets

(51) Int. Cl.

| | |
|---|---|
| *A61B 18/00* | (2006.01) |
| *A61B 18/14* | (2006.01) |
| *A61F 2/24* | (2006.01) |
| *A61M 25/09* | (2006.01) |
| *A61M 29/02* | (2006.01) |

(52) U.S. Cl.
CPC ........ *A61B 18/1492* (2013.01); *A61F 2/2476* (2020.05); *A61M 25/09* (2013.01); *A61M 29/02* (2013.01); *A61B 2017/3425* (2013.01); *A61B 2018/00511* (2013.01); *A61B 2018/00595* (2013.01)

(58) Field of Classification Search
CPC ............ A61B 18/1492; A61B 17/3415; A61B 17/3417; A61B 17/3423; A61B 17/3468; A61B 17/3478; A61B 2017/3425; A61B 2090/064; A61M 25/09; A61M 29/02; A61F 2/2476
See application file for complete search history.

(56) References Cited

U.S. PATENT DOCUMENTS

| | | | | |
|---|---|---|---|---|
| 11,331,421 | B2 | 5/2022 | Kapur | |
| 11,400,263 | B1* | 8/2022 | Arepally | A61M 25/10 |
| 12,186,469 | B2 | 1/2025 | Kapur | |
| 2001/0012950 | A1* | 8/2001 | Nishtala | A61M 25/0662 |
| | | | | 606/198 |
| 2005/0125021 | A1* | 6/2005 | Nance | A61M 31/005 |
| | | | | 604/103.05 |
| 2006/0079859 | A1 | 4/2006 | Elkins et al. | |
| 2007/0225702 | A1* | 9/2007 | Kaouk | A61B 17/320016 |
| | | | | 606/49 |
| 2008/0255642 | A1* | 10/2008 | Zarins | A61N 5/0601 |
| | | | | 607/99 |
| 2010/0125288 | A1* | 5/2010 | Gelfand | A61B 5/6846 |
| | | | | 606/158 |
| 2012/0123461 | A1* | 5/2012 | Gillies | A61B 17/3423 |
| | | | | 604/164.01 |
| 2013/0274783 | A1* | 10/2013 | Wynberg | A61B 17/3421 |
| | | | | 606/185 |
| 2014/0221964 | A1* | 8/2014 | Xiao | A61M 25/0082 |
| | | | | 604/504 |
| 2015/0297139 | A1* | 10/2015 | Toth | A61B 5/388 |
| | | | | 600/373 |
| 2017/0252548 | A1 | 9/2017 | Krimsky | |
| 2018/0193618 | A1 | 7/2018 | Erbey, II et al. | |
| 2018/0344994 | A1* | 12/2018 | Karavany | A61M 60/33 |
| 2020/0206472 | A1* | 7/2020 | Ma | A61M 29/02 |
| 2022/0280709 | A1 | 9/2022 | Kapur | |

OTHER PUBLICATIONS

Zhu G, Wu D, Wu K, Song W, Yang Z, Zhang Y, Zhang L, He D. The Retroperitoneal Laparoscopic Renal Capsulectomy for Spontaneous Renal Subcapsular Fluid Collection: A Case-Series Report and Literature Review. Medicine (Baltimore). May 2016;95(21):e3751. doi: 10.1097/MD.0000000000003751. (Year: 2016).*

Meyrier, A.Y. (2005). Transjugular renal biopsy. Update on hepato-renal needlework. Nephrology, dialysis, transplantation : official publication of the European Dialysis and Transplant Association—European Renal Association, 20 7, 1299-302. (Year: 2005).*

Merit-Maestro®-microcatheter-IFU.pdf. (Oct. 5, 2017). https://www.merit.com/wp-content/uploads/2018/10/Merit-Maestro%C2%AE-Microcatheter-IFU.pdf (Year: 2017).*

Abildgaard, et al., "Renal Vascular Adjustments to Partial Renal Venous Obstruction in Dog Kidney," Circ. Res., 61(2):194-202 (Aug. 1987).

Bracey, "Acute Renal Failure; Two Cases Treated by Decapsulation and Peritoneal Dialysis," Br. J. Surg., 38(152):482-488 (Apr. 1951).

Calasi, R.E., M.D., "Kidney Decapsulation and Acute Renal Failure," Ann, Surg., 187(4):441-442 (Apr. 1978).

Cruces et al., "Renal Decapsulation Prevents Intrinsic Renal Compartment Syndrome in Ischemia-Reperfusion-Induced Acute Kidney Injury: A Physiologic Approach," Crit. Care Med., 46(2):216-222 doi: 10.1097/CCM.0000000000002830 (Feb. 2018).

Culpepper, et al., "Renal Decapsulation for Oliguria and Anuria," Am. J. Med. Sci., 124(1):100-108 (Jul. 1947).

Evans, R.G. "Renal Decapsulation to Treat Ischemic Acute Kidney Injury: A New Twist in an Old Tale," Crit. Care Med., 46(2):332-333 doi: 10.1097/CCM.0000000000002861 (Feb. 2018).

Extended European Search Report dated Dec. 23, 2022 in EP Patent Appl. No. 20805862.8 (013001).

Felber, "Renal Decapsulation," The Journal of the Medical Association of Georgia, 35:7-9 (Jan. 1946).

Gewertz, "Effect of Renal Decapsulation on Cortical Hemodynamics in the Postischemic Kidney," J. Surg. Res., 28(3):252-259 (Mar. 1980).

Herbert, "Effect of Renal Decapsulation on Renal Function," Am. J. Physiol., 229(3):632-639 (Sep. 1975).

International Search Report & Written Opinion dated Aug. 6, 2020 in Int'l PCT Patent Appl. Serial No. PCT/US20/32523 (011001).

Khraibi, et al., "Effect of acute renal decapsulation on pressure natriuresis in SHR and WKY rats," Am. J Physiol., 257(5 Pt 2): F785-9 (Nov. 1989).

Khraibi, et al., "Effect of renal decapsulation on renal interstitial hydrostatic pressure and natriuresis," Am. J Physiol., 257(1 Pt 2): F44-8 (Jul. 1989).

Lowe, "Renal Decapsulation in the Treatment of Oliguria and Anuria," US Nav. Med. Bull., 47(6):959-964 (Nov.-Dec. 1947).

Newman, D. M.B., "Decapsulation of the Kidney for the Treatment of Albuminuria," Br. Med. J., 1(2261):1011-1012 (Apr. 1904).

Nichol, J.E., "Indications for Decapsulation of the Kidney," Can. Med. Assoc. J., 43(6):577-580 (Dec. 1940).

Slegers, et al., "Influence of Renal Capsule on Kidney Function in Hypertension," Clin Exp Hypertens A, 7(12):1751-1768 (1985-1986).

Stone, H.H., M.D., "Renal Decapsulation in the Prevention of Post-ischemic Oliguria," Ann. Surg., 186(3):343-355 (Sep. 1977).

Stothert, C.S. Jr. M.D., "Renal Blood Flow and Intrarenal Distribution of Blood Flow After Decapsulation in the Postischemic Kidney," Ann Surg., 191(4):456-459 (Apr. 1980).

Stothert, "Evaluation of Decapsulation of the Canine Kidney on Renal Function Following Acute Ischemia," J. Surg. Res., 26(5):560-564 (May 1979).

Vermeulen, et al., Effect of Renal Decapsulation in Experimental Mercury Nephrosis,: J. Urol., 60(2):216-220 (Aug. 1948).

\* cited by examiner

100

| Advance guidewire to position within subcapsular space of renal capsule | 102 |

↓

| Advance catheter via guidewire to position within subcapsular space | 104 |

↓

| Perform diagnostic and/or therapeutic procedure within subcapsular space | 106 |

400

Create puncture within fibrous capsule of renal capsule — 402

Dilate puncture within fibrous capsule of renal capsule — 404

Anchor spacer within dilated puncture in fibrous capsule of renal capsule — 406

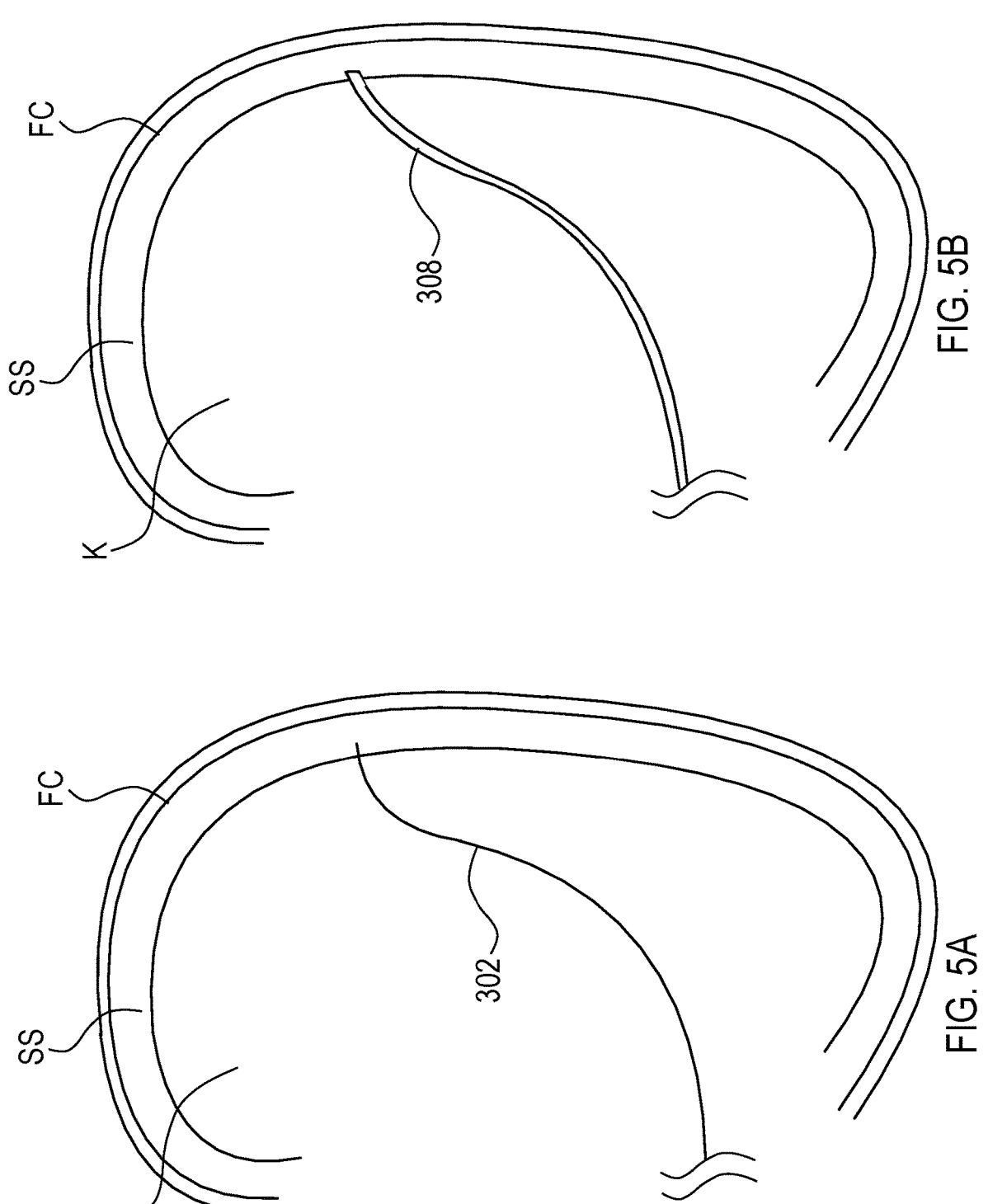

700

1100 c-ro1-15 ecmo 100-... 190117135363....Renal C.

SYSTEMS AND METHODS FOR ACCESSING A RENAL CAPSULE FOR DIAGNOSTIC AND THERAPEUTIC PURPOSES

CROSS-REFERENCE TO RELATED APPLICATIONS

This application is a national phase application under 35 U.S.C. § 371 of PCT/US2020/032523, filed May 12, 2020, which claims the benefit of priority of U.S. Provisional Patent Application No. 62/847,781, filed May 14, 2019, the entire contents of each of which are incorporated herein by reference.

FIELD OF THE INVENTION

This application relates generally to systems and methods of accessing the subcapsular space of a patient's kidney in a minimally invasive and/or catheter-based manner for therapeutic and/or diagnostic purposes such as to sense and reduce organ pressure, deliver therapies, and/or disrupt the capsule (decapsulation) in patients with heart failure to, e.g., treat renal dysfunction.

BACKGROUND

Heart performance and kidney function are closely interconnected. One of the most important comorbidities in heart failure is renal dysfunction such as renal failure or renal insufficiency. At least one in four patients hospitalized for acute decompensated heart failure has significant renal dysfunction. Renal insufficiency is a major cause of morbidity and mortality in patients with heart failure, shock, or cardiovascular compromise. Renal insufficiency occurs when the kidneys function poorly, which may be due to reduced blood-flow or perfusion through the kidneys caused by either low renal artery blood pressure or a build-up of pressure in the renal vein, known as congestion. Heart failure is associated with both low renal artery blood pressure and renal vein congestion, and is therefore a major cause of renal failure known as cardiorenal syndrome. Since the kidneys remove fluid from the body, primary kidney failure can also cause heart failure by triggering volume overload which may overwhelm an already impaired heart.

Renal function may be impaired due to, e.g., low or excessively high arterial perfusion, venous congestion, increased intra-abdominal pressure, and ureteral obstruction. Prior studies have shown that increases in intra-abdominal pressure increase extrinsic compression of the kidney and the bladder. Further, congestion of the renal veins has also been associated with a build-up of pressure within the kidney itself. Since the kidney is housed within a fibrous capsule, there is limited room for the kidney to expand once it becomes engorged with blood, which may lead to extravasation of excess fluid within the renal capsule. As a result, the pressure within the capsule increases, compressing the kidney, which may contribute to worsening kidney function. Under normal conditions, the kidneys regulate body fluid and blood pressure, as well as regulate blood chemistry and remove organic waste. When the kidneys receive low blood flow, as occurs in patients with heart failure, the brain interprets this as a sign of dehydration, and causes the kidneys to release hormones that stimulate the body to retain sodium and water, thus contributing to worsened heart and renal failure. This may also lead to poor kidney function, or kidney failure that requires dialysis.

Devices and methods for reducing intra-renal pressures have been contemplated. For example, U.S. Patent Publication No. 2018/0193618 to Erbey describes creating negative pressure in the urinary tract to facilitate urine production and to extract urine from the patient. Specifically, Erbey requires a ureteral stent that extends between the ureter and the bladder to maintain patency of fluid flow between kidney and bladder, and a bladder catheter disposed in the bladder and coupled to an external pump that creates the negative pressure and extracts urine from the bladder.

In addition, U.S. Pat. No. 6,231,551 to Barbut describes introducing a constrictor through the femoral artery into the renal artery and expanding the constrictor to partially occlude blood flow from descending aorta to renal arteries, thereby reducing blood pressure distal to the occlusion. However, the constrictor of Barbut is designed to be surgically implanted, which poses risks of iatrogenic injury. Moreover, U.S. Patent Publication No. 2010/0125288 to Gelfand describes a controllably adjustable renal constriction device for partial occlusion of the renal artery to reduce renal perfusion pressure to treat chronic renal failure. Gelfand requires external screws to clamp down to restrict renal arterial blood flow.

However, none of these approaches involve the renal capsule. A major limitation of capsule-based therapeutic approaches has been the inability to access the renal capsule without major surgery. For example, prior reports have shown that surgical removal of the renal capsule improves kidney function; however, no one has developed a method to perform decapsulation without surgery or via percutaneous catheter-based approaches. Thus, there is a need for systems and methods to access the renal capsule in a minimally invasive and/or catheter-based manner.

Example publications include: Cruces, et al., "Renal Decapsulation Prevents Intrinsic Renal Compartment Syndrome in Ischemia-Reperfusion-Induced Acute Kidney Injury: A Physiologic Approach," Crit Care Med. 2018 February; 46(2): 216222. doi: 10.1097/CCM.0000000000002830; Evans, "Renal Decapsulation to Treat Ischemic Acute Kidney Injury: A New Twist in an Old Tale," Crit Care Med. 2018 February; 46(2):332-333. doi: 10.1097/CCM.0000000000002861; Khraibi, et al. "Effect of acute renal decapsulation on pressure natriuresis in SHR and WKY rats," Am J Physiol. 1989 November; 257(5 Pt 2): F785-9; Khraibi, et al. "Effect of renal decapsulation on renal interstitial hydrostatic pressure and Natriuresis," Am J Physiol. 1989 July; 257(1 Pt 2):R44-8; Abildgaard, et al. "Renal vascular adjustments to partial renal venous obstruction in dog kidney," Circ Res. 1987 August; 61(2):194-202; Slegers, et al. "Influence of renal capsule on kidney function in hypertension," Clin Exp Hypertens A. 1985-1986; 7(12): 1751-68; Stothert, "Renal blood flow and intrarenal distribution of blood flow after decapsulation in the postischemic kidney," Ann Surg. 1980 April; 191(4):456-9; Gewertz, "Effect of renal decapsulation on cortical hemodynamics in the postischemic Kidney," J Surg Res. 1980 March; 28(3): 252-9; Stothert, "Evaluation of decapsulation of the canine kidney on renal function following acute ischemia," J Surg Res. 1979 May; 26(5):560-4; Calasi, "Kidney decapsulation and acute renal failure," Ann Surg. 1978 April; 187(4):441-2; tone, et al. "Renal decapsulation in the prevention of post-ischemic oliguria," Ann Surg. 1977 September; 186(3): 343-55; Hebert, "Effect of renal decapsulation on renal function," Am J Physiol. 1975 September; 229(3):632-9; Bracey, "Acute renal failure; two cases treated by decapsulation and peritoneal dialysis," Br J Surg. 1951 April; 38(152):482-8; Vermeulen, et al. "Effect of renal decapsulation in experimental mercury nephrosis," J Urol. 1948 August; 60(2):216-20; Lowe, "Renal decapsulation in the treatment of oliguria and anuria," U S Nav Med Bull. 1947 November-December; 47(6):959-64; Raines, "Renal decapsulation in the treatment of anuria," Memphis Med J. 1947 September; 22(9):140-3; Culpepper, et al. "Renal decapsulation for oliguria and anuria" Am J Med Sci. 1947 July; 124(1):100-8; Felber, "Renal decapsulation," J Med Assoc Ga. 1946 January; 35:7-9; Nichol, "Indications for Decapsulation of the Kidney," Can Med Assoc J. 1940 December; 43(6):577-80; Newman, "Decapsulation of the Kidney for the Treatment of Albuminuria," Br Med J. 1904 Apr. 30; 1(2261):1011-2.

There exists a need to access the renal capsule in a minimally invasive and/or catheter-based manner, for example, to effectively decapsulate kidneys. For example, there exists a need to reduce intra-renal pressures to restore and improve renal function.

SUMMARY OF THE INVENTION

The present invention provides systems and methods for accessing a subcapsular space of the renal capsule of a patient. The "subcapsular space" is a fluid-filled space between the kidney and a fibrous capsule surrounding the kidney. The fibrous capsule and the subcapsular space are collectively the "renal capsule."

In a preferred embodiment, the subcapsular space of the patient's kidney is accessed in a minimally invasive manner for therapeutic and/or diagnostic purposes. For example, the method includes intravascularly advancing a guidewire to a position adjacent to the subcapsular space of the renal capsule of the patient's kidney, and intravascularly advancing a distal end of a catheter via the guidewire to position the distal end of the catheter into the subcapsular space of the renal capsule of the patient's kidney, e.g., via arterial, venous, or lymphatic vessels. The catheter may include a diagnostic and/or therapeutic portion at the distal end for diagnostic(s) and/or delivering therapy(ies) within the subcapsular space of the kidney. In accordance with another aspect of the present invention, a non-vascular approach may be employed by accessing the kidney through the bladder and ureters, or transcutaneously. A transcutaneous approach may be performed by general surgeons and/or interventional radiologists, and may avoid vascular compromise.

In accordance with yet another aspect of the present invention, the subcapsular space may be accessed using a percutaneously delivered catheter-based approach. With access to the renal capsule, the catheter may be used to perform a variety of procedures to diagnose and/or treat conditions such as renal dysfunction and heart failure. Exemplary procedures include decapsulating the renal capsule and/or directly removing fluid from of the subcapsular space to relieve renal pressure, measuring renal pressure build-up and/or accumulating biomarkers of renal function/injury within the kidney, and/or delivering drug therapy to the renal capsule.

The systems and methods are able to access the renal capsule in a manner to diagnose/monitor increased renal capsule pressure, and to improve kidney function. For example, the systems and methods described herein may deliver sensors to detect a build-up of pressure inside the subcapsular space of the renal capsule of the kidney and alert the patient or physician that a decrease in renal pressure is required. Additionally, or alternatively, the systems and methods may deliver drugs into the renal capsule that specifically target kidney function by reducing kidney fibrosis and/or enhancing fluid removal with diuretics, or to treat localized diseases such as kidney cancer, or any combination thereof. Additionally, or alternatively, the systems and methods may deliver at least one of stem cells, viruses for gene therapy, RNAi, nanoparticles, or dyes in the subcapsular space. Additionally, or alternatively, the systems and methods may deliver a device that disrupts the renal capsule (decapsulation), thereby allowing for expansion of the kidney when engorged and averting any injury to the kidney due to pressure build up.

In accordance with one aspect of the present invention, a system for accessing a subcapsular space of a renal capsule of a patient's kidney is provided. The system includes a guidewire that may be advanced to a position within the subcapsular space of the renal capsule from within the kidney, and a catheter having an elongated shaft having a distal region, a proximal region, and a lumen sized and shaped to receive the guidewire extending therebetween. The distal region of the catheter is sized and shaped to be disposed within the subcapsular space for performing a diagnostic or therapeutic procedure, or both.

In accordance with one aspect of the present invention, the distal region of the catheter is further structured to form a puncture in a fibrous capsule surrounding the subcapsular space of the renal capsule to access a space outside the fibrous capsule, e.g., the retro-peritoneal cavity. For example, the catheter or wire may have a sharp tip, or the catheter may be a wire having an electrocautery for dissecting the fibrous capsule to form the puncture in the fibrous capsule. Accordingly, the system further may include a dilation catheter having an expandable member, e.g., a balloon, disposed thereon, the expandable member constructed to be advanced to the puncture in the fibrous capsule and to dilate the puncture to a dilated size. The system also may include a spacer device that may be anchored into the dilated puncture of the fibrous capsule to maintain the dilated size of the puncture. For example, the dilated puncture relieves intra-parenchymal pressure within the kidney, thereby improving renal function. The spacer device may have a one-way valve disposed therein.

In accordance with another aspect of the present invention, the system further includes a sensor sized and shaped to be disposed in the subcapsular space via the catheter to measure a physiological parameter, e.g., renal capsule pressure, and which may generate a signal indicative of the measured physiological parameter. For example, the sensor may be a sensor wire or a chip. Accordingly, the system further may include a non-transitory computer readable media having instructions stored thereon that, when executed by a processor of an external computer operatively coupled to the sensor, cause the processor to receive and process the signal indicative of the measured physiological parameter. For example, the signal(s) may be received remotely via, e.g., a wired or wireless communication using a CardioMEMS system (available by CardioMEMS, Atlanta, Georgia). The non-transitory computer readable media further may include instructions stored thereon that, when executed by the processor of the external computer, cause the processor to compare the measured physiological parameter based on the signal with a threshold physiological parameter stored in a memory of the processor, and cause the external computer to generate an alert if the measured physiological parameter is above the threshold physiological parameter.

In accordance with yet another aspect of the present invention, the catheter is structured to deliver at least one of a drug, stem cells, viruses for gene therapy, RNAi, nanoparticles, or dyes into the subcapsular space. For example, the drug may reduce kidney fibrosis, enhance fluid removal with diuretics, or treat localized diseases such as cancer, or any combination thereof. In accordance with yet another aspect of the present invention, the catheter includes an expandable member, e.g., a balloon, disposed on the distal region of the catheter. The expandable member is structured to expand within the subcapsular space of the renal capsule to displace and stretch the fibrous capsule surrounding the kidney, enlarging the subscapular space.

In accordance with another aspect of the present invention, a method for accessing a subcapsular space of a renal capsule of a patient's kidney is provided. The method includes advancing the guidewire to the position within the subcapsular space of the renal capsule of the patient's kidney, advancing the distal end of a catheter via the guidewire such that the distal end of the catheter is disposed within the subcapsular space of the renal capsule, and performing a diagnostic or therapeutic procedure, or both, within the subcapsular space using the catheter.

When the distal end of the catheter is structured to form a puncture in a fibrous capsule, the method further may include puncturing the fibrous capsule via the distal end of the catheter to form a puncture in the fibrous capsule; delivering the dilation catheter to the puncture of the fibrous capsule; actuating the expandable member within the puncture to dilate the puncture of the fibrous capsule to the dilated size; and anchoring the spacer device within the dilated puncture of the fibrous capsule to maintain the dilated size of the puncture.

When the catheter is used to dispose a sensor in the subcapsular space, the method further may include measuring a physiological parameter, e.g., renal pressure, within the subcapsular space via the sensor; and generating a signal indicative of the measured physiological parameter. In accordance with one aspect of the present invention, the method further may include receiving the signal indicative of the measured physiological parameter via the external computer operatively coupled to the sensor. Accordingly, the method may include comparing the measured physiological parameter based on the signal with a threshold physiological parameter, and generating an alert if the measured physiological parameter is above the threshold physiological parameter.

In accordance with another aspect of the present invention, the method further may include receiving the signal indicative of the measure physiological parameter via a device configured to impact blood flow within the patient's kidney. Alternatively, or additionally, the method may include generating a feedback signal based on the received signal indicative of the measure physiological parameter. When the catheter is structured to displace the fibrous capsule from the kidney, the method further may include expanding an expandable member disposed on the distal end of the catheter to displace the fibrous capsule surrounding the kidney, collapsing the expandable member, and removing the catheter and expandable member from the subcapsular space.

When the catheter is structured to deliver a drug into the subcapsular space, the method further may include delivering the drug into the subcapsular space of the renal capsule via the catheter. The method also may include directly removing fluid from within the subcapsular space through the distal end of the catheter and collecting the fluid outside the patient's body to directly reduce renal pressure.

BRIEF DESCRIPTION OF THE DRAWINGS

FIGS. 5A-5G illustrate steps taken during the method of FIG. 4, according to some embodiments of the present invention.

DETAILED DESCRIPTION

The renal capsule includes a fibrous capsule surrounding the kidney, and a subcapsular fluid-filled space between the kidney and the fibrous capsule. Embodiments of the present invention are directed to exemplary systems and methods for accessing the subcapsular space of the renal capsule of a patient's kidney. Instead of requiring a major surgery to access the subcapsular space, the present invention is minimally invasive and accesses the subcapsular space from within the kidney, e.g., intravascularly via a blood vessel such as arterial, venous, or lymphatic vessels or non-vascularly via the bladder and ureter or transcutaneously. Alternatively, or additionally, the subcapsular space may be accessed using a percutaneously delivered catheter-based approach.

Figure 1:
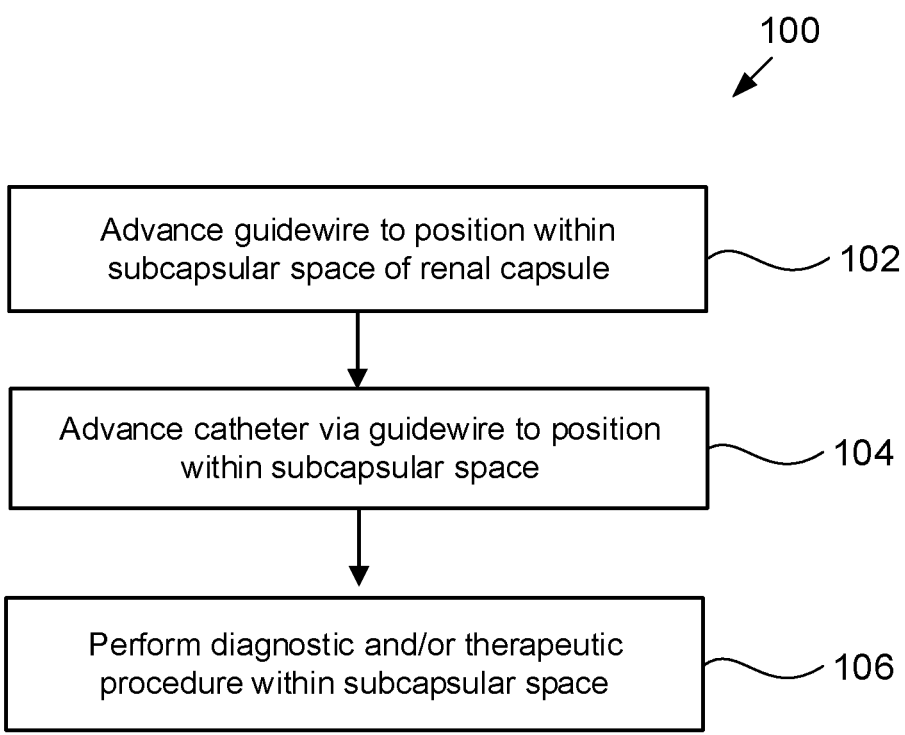
FIG. 1 is a flow chart of steps in an exemplary method for accessing the subcapsular space of a patient's renal capsule in accordance with the principles of the present invention.

Referring now to FIG. 1, an exemplary method 100 for accessing a subcapsular space of a renal capsule of a patient's kidney is provided. At step 102, a guidewire is advanced to a position within the subcapsular space surrounding the patient's kidney from within the kidney. Various approaches may be used to deliver the guidewire to the target site. For example, the guidewire may be inserted via a transvenous approach through the renal vein of the patient, a transarterial approach through a renal artery of the patient, or a transureteral approach through the bladder and ureter of the patient. At step 104, the distal region of a catheter, e.g., a micro-catheter, is advanced via the guidewire, such that the distal end of the catheter enters and is positioned within the subcapsular space. Once access is provided to within the subcapsular space of the renal capsule, at step 106, numerous diagnostic and/therapeutic procedures may be performed, as described in further detail below. For example, procedures may be performed to treat conditions such as heart failure including, but not limited to, therapeutic procedures, e.g., ablation, disrupting at least a portion of the renal capsule (decapsulation), displacing the fibrous capsule from the kidney, and/or directly removing fluid from of the subcapsular space to relieve renal pressure, and/or delivering drug therapy to the renal capsule, and diagnostic procedures, e.g., measuring physiological parameters such as build-up of renal pressure within the kidney and/or accumulating biomarkers of renal function/injury, e.g., lactate, and/or visualizing the subcapsular space.

Figures 2A, 2B, 2C, 2D:
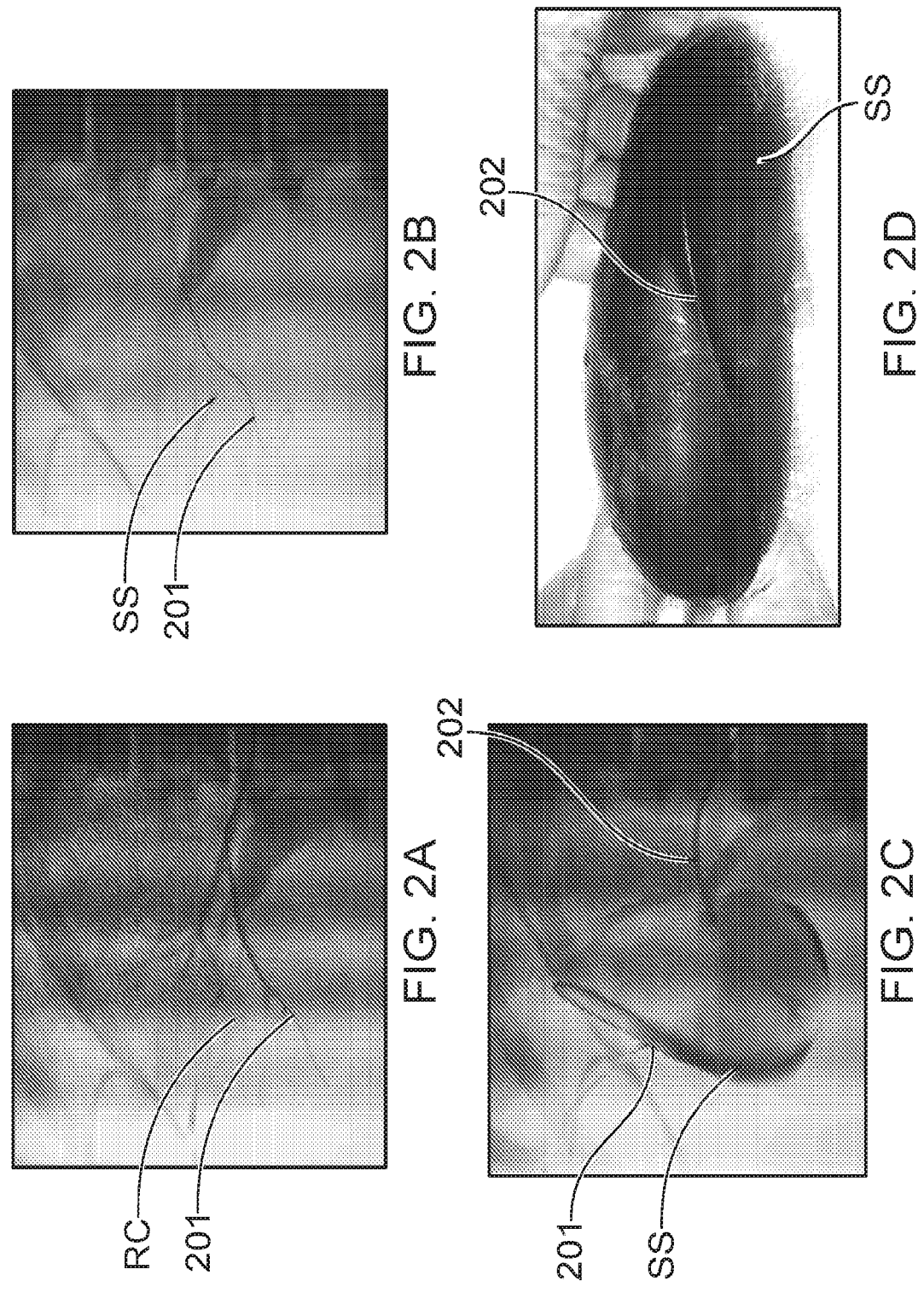
FIGS. 2A-2H illustrate proof-of-concept of the principles of the present invention.

Referring now to FIGS. 2A-2H, proof-of-concept of the principles of the present invention is provided. For example, FIG. 2A illustrates wire 201, e.g., a 0.018" wire, advanced within renal cortex RC of a kidney. FIG. 2B illustrates penetration of subcapsular space SS by wire 201. FIG. 2C illustrates wire 201 disposed within subcapsular space SS with a contrast agent, and catheter 202 being advanced over wire 201. FIG. 2D illustrates a kidney having catheter 202 disposed within subcapsular space SS of the renal capsule with a contrast agent. Specifically, FIG. 2D is an image showing blue dye injected within subcapsular space SS under a capsule of a kidney in accordance with the principles of the present disclosure. As shown in FIG. 2D, the blue dye is restricted to subcapsular space SS, thereby confirming that materials introduced into subcapsular spaces SS using the systems and methods described herein will stay subcapsular.

Figure 2E:
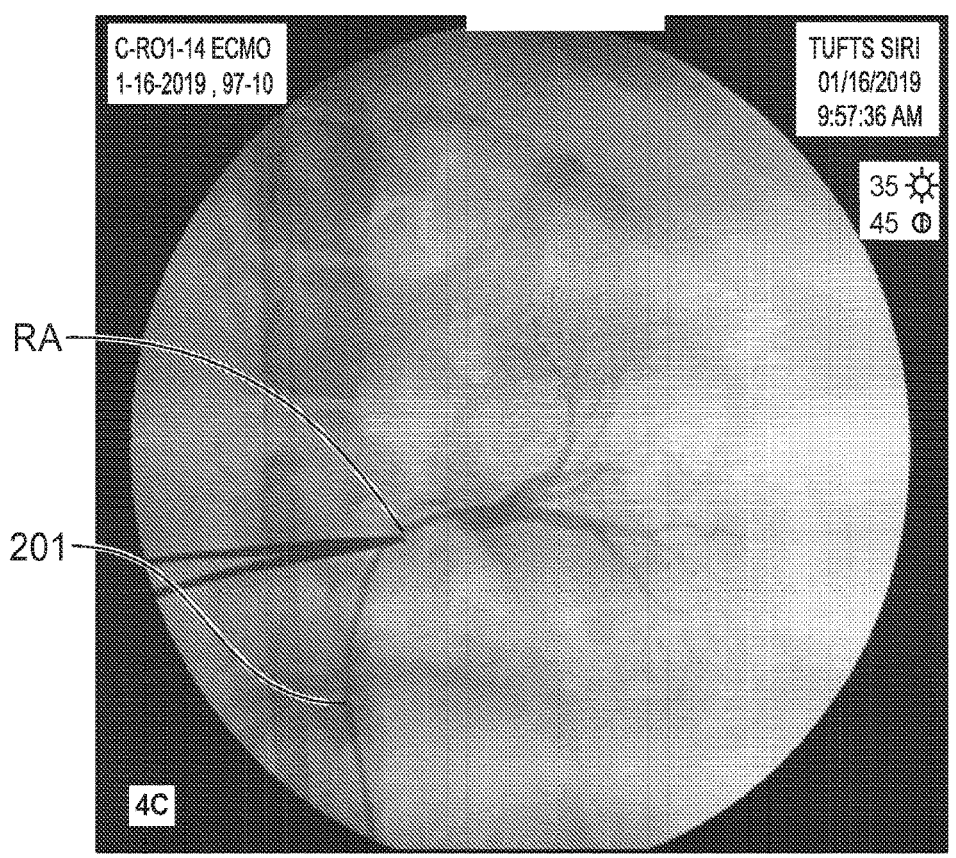
Figure 2F:
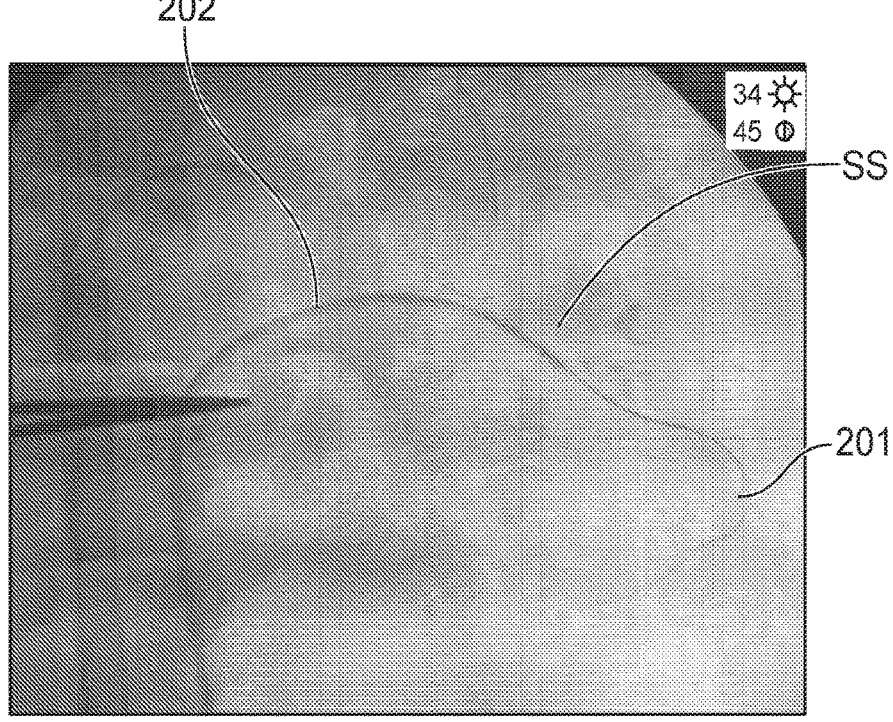
Figure 2G:
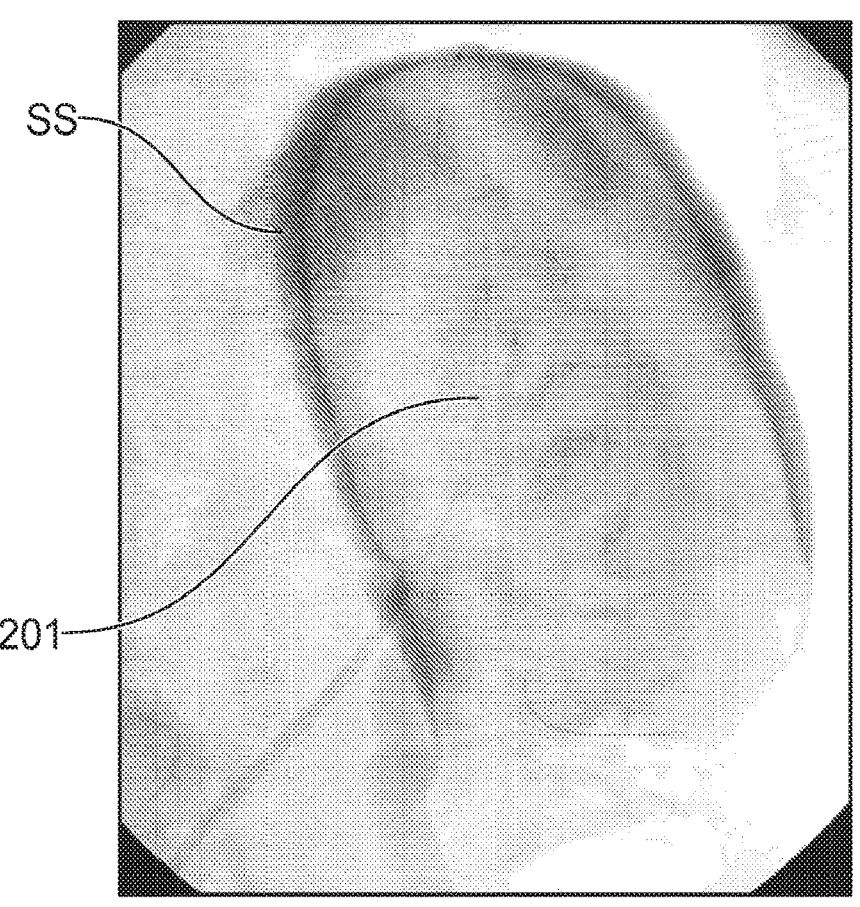
Figure 2H:
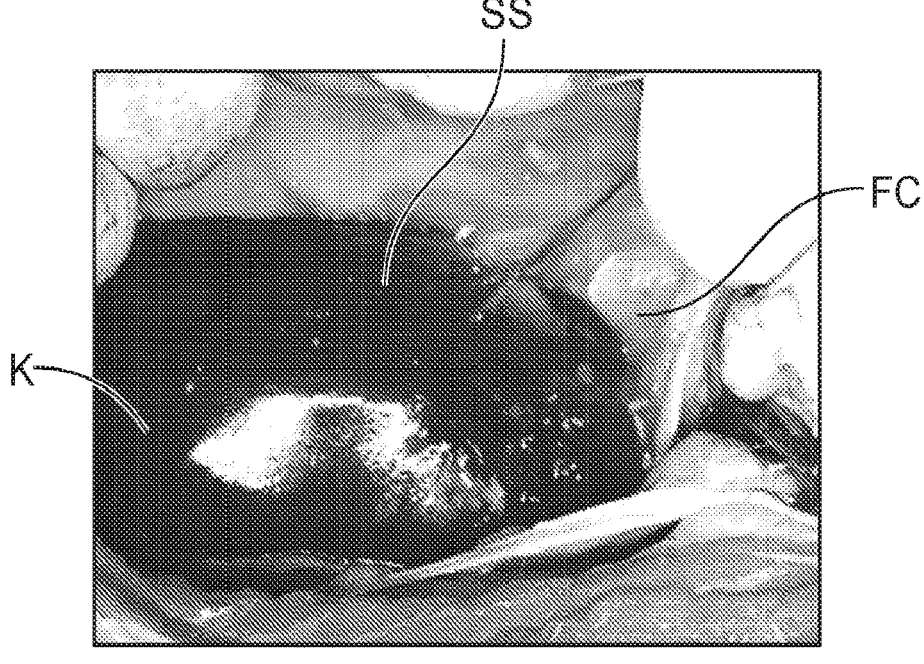

Additionally, FIG. 2E illustrates an arterial delivery approach where wire 201 is advanced through renal artery RA, and FIG. 2F illustrates wire 201 subsequently disposed within subcapsular space SS of the renal capsule, with catheter 202 advanced over wire 201. FIG. 2G illustrates wire 201 disposed around the kidney within subcapsular space SS of the renal capsule (denoted by the darker contrast). FIG. 2H is an image showing blue dye injected within subcapsular space SS under fibrous capsule FC of kidney K in accordance with the principles of the present disclosure. Similar to FIG. 2D, this image shows that the subcapsular space has been successfully accessed in accordance with the principles of the present invention as evidenced by the blue dye fully contained within and restricted to subcapsular space SS between fibrous capsule FC and kidney K of a rodent model, thereby again confirming that materials introduced into subcapsular space SS using the systems and methods described herein will stay subcapsular.

As described above, with access to the subcapsular space of the renal capsule, numerous diagnostic and/therapeutic procedures may be performed such as disruption of at least a portion of the renal capsule (decapsulation) to relieve renal pressure. For example, a system may be used to create a puncture within the fibrous capsule of the renal capsule to decapsulate the kidney, and to deliver a spacer to maintain the puncture to relieve renal pressure of the kidney. The spacer may include a one-way valve to regulate pressure relief across the fibrous capsule.

Figure 3:
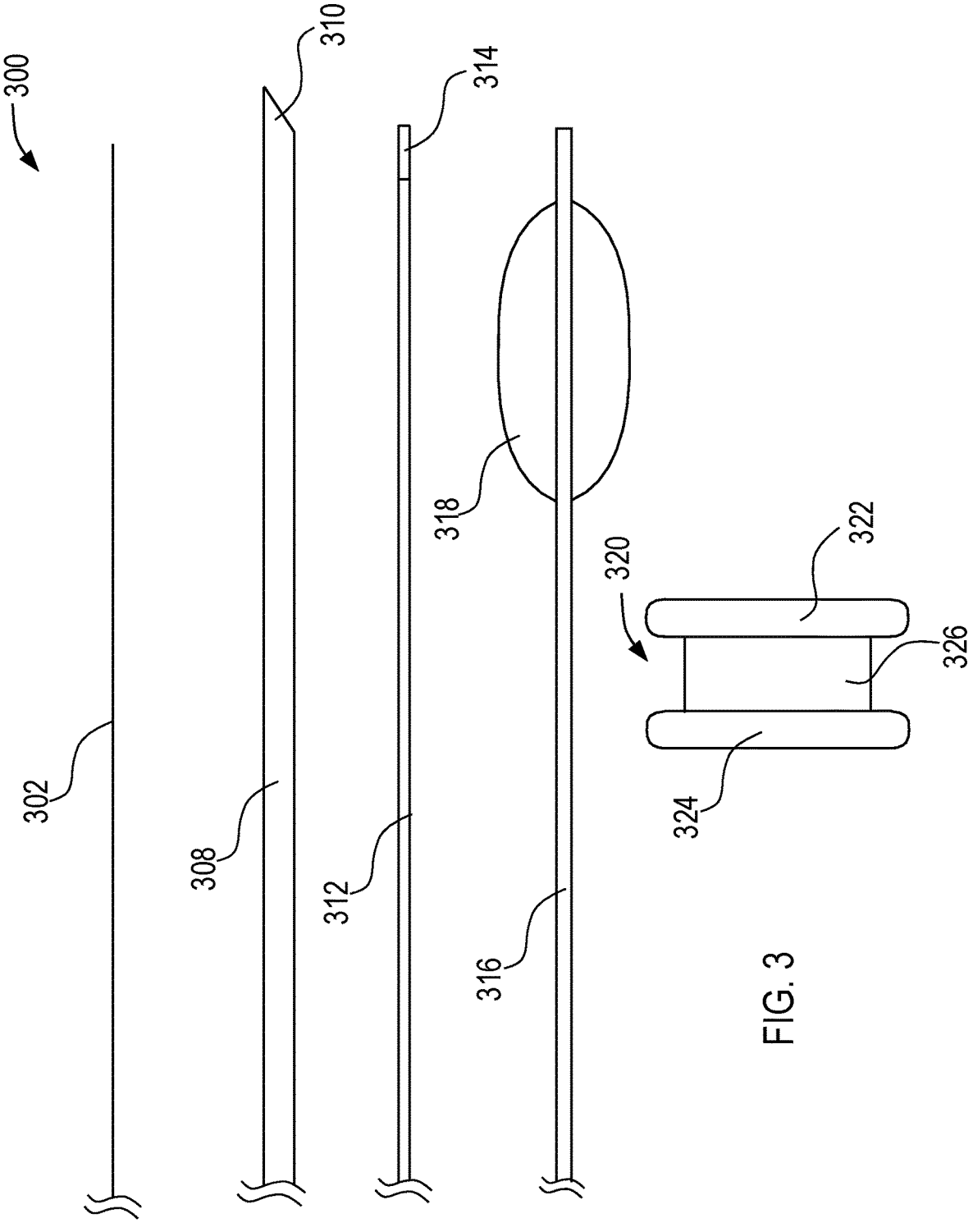
FIG. 3 illustrates an exemplary system for decapsulating a kidney of a patient in accordance with the principles of the present invention.

Referring now to FIG. 3, a system for decapsulating a renal capsule of a patient's kidney in accordance with the principles of the present invention is provided. System 300 includes guidewire 302, catheter 308 or catheter 312, e.g., a micro-catheter, dilation catheter 316, and spacer device 320. The physician may select between catheter 308 and 312 depending on the needs of the patient. Catheters 308 and 312 both have a lumen sized and shaped to receive guidewire 302 therethrough. In addition, catheter 308 and catheter 312 have distal ends that are sized and shaped to be disposed within the subcapsular space of the renal capsule. Catheter 308 has sharp tip 310 disposed on its distal end. Sharp tip 310 is constructed to cut through the target tissue for decapsulation, e.g. the fibrous capsule of the renal capsule of the kidney, to create a puncture therethrough to disrupt the integrity of the fibrous capsule and thereby reduce intraparenchymal renal pressure. For example, sharp tip 310 may be a blade or needle tip. Alternatively, system 300 may include catheter 312 instead of catheter 308. Catheter 312 is a wire with electrocautery having electrode tip 314 which permits a direct or alternating current to be passed through the resistant metal wire electrode to generate heat. The heated electrode tip 314 may then be applied to the target tissue to dissect the target tissue and create a puncture therethrough.

Dilation catheter 316 includes expandable member 318 disposed at its distal region. Expandable member 318 may be expanded to a desired sized to dilate the puncture created by catheter 308 or 312 to a desired dilation size. For example, expandable member 318 may be an inflatable balloon that is transitionable between a deflated delivery state and an inflated dilation state via fluid introduced through a fluid port positioned within the expandable balloon in fluid communication with a fluid lumen of dilation catheter 316. Accordingly, the proximal end of dilation catheter 316 may be coupled to a fluid source outside of the patient's body. As will be understood by a person having ordinary skill in the art, expandable member 318 may be any other expandable device known in the art, such as an expandable cage that is capable of exerting the required amount force to dilate the puncture in the fibrous capsule of the kidney to create a puncture therethrough.

Spacer device 320 is designed to maintain the dilated puncture created in the fibrous capsule of the renal capsule, and to permit fluid communication between the subcapsular space of the renal capsule and the space outside the fibrous capsule. Thus, spacer device 320 has a central opening extending therethrough from proximal end 322 to distal end 324 of spacer device 320. Proximal end 322 and distal end 324 are constructed to anchor space device 320 within the puncture of the fibrous capsule, and may form a seal such that fluid only flows across spacer device 320 through its central opening. For example, proximal end 322 and distal end 324 may protrude outward a greater distance than intermediate section therebetween, as illustrated. In addition, spacer device 320 is transitionable from a collapsed delivery state, e.g., within an introductory sheath, where it may be advanced over guidewire 302 via a delivery catheter, to an expanded deployed state, e.g., upon retraction of the introductory sheath, where it may be anchored within the puncture of the fibrous capsule.

Figure 4:
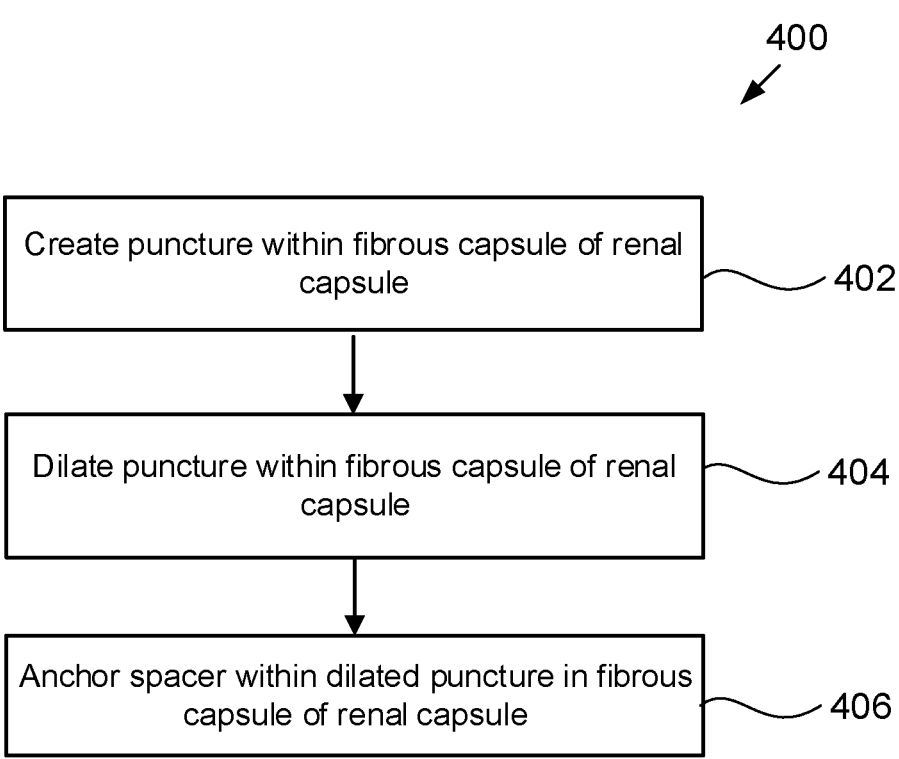
FIG. 4 is a flow chart of steps in an exemplary method for decapsulating a kidney of a patient in accordance with the principles of the present invention.
Figures 5C, 5D:
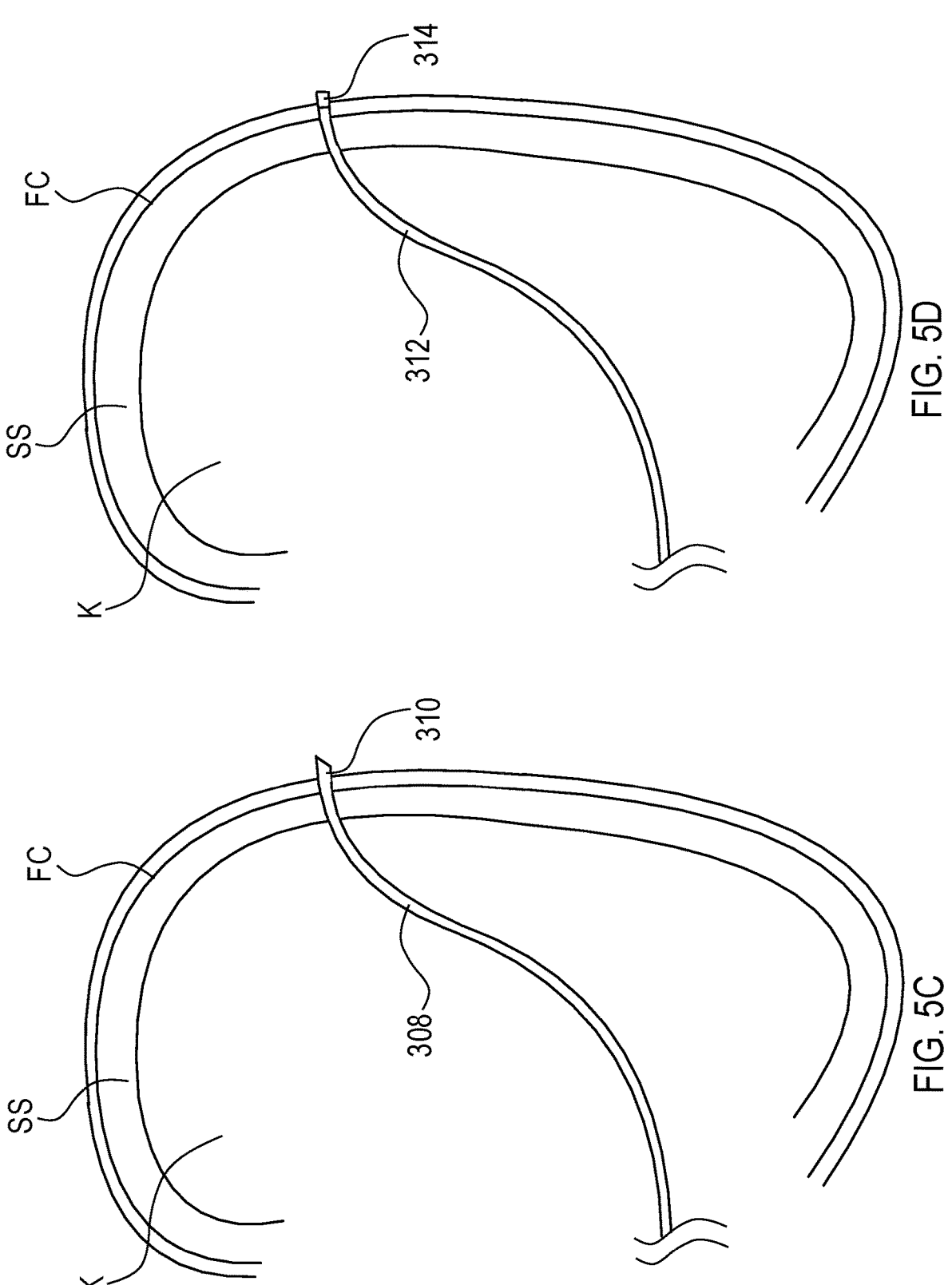

Referring now to FIG. 4, an exemplary method for performing a therapeutic procedure (step 106 of FIG. 1) is provided. Specifically, method 400 for decapsulating a renal capsule of a patient's kidney using system 300 is provided. Some of the steps of method 400 may be further elaborated by referring to FIGS. 5A-5G. First, as shown in FIG. 5A, guidewire 302 is advanced to a position within subcapsular space SS surrounding kidney K from within kidney (step 102 of FIG. 1). As described above, various approaches may be used to deliver guidewire 302 to the target site, e.g., via a transvenous approach through the renal vein of the patient, a transarterial approach through a renal artery of the patient, or a transureteral approach through the bladder and ureter of the patient. Next, the distal region of catheter 308 and/or catheter 312 is advanced via guidewire 302, such that the distal end of catheter 308 and/or catheter 312 enters and is positioned within subcapsular space SS as illustrated in FIG. 5B (step 104 of FIG. 1).

At step 402, a puncture is created within fibrous capsule FC. When catheter 308 is selected, sharp tip 310 of catheter 308 engages fibrous capsule FC with a force sufficient to penetrate fibrous capsule FC to form a puncture therein as illustrated in FIG. 5C. When catheter 312 is selected, electrode tip 314 is advanced to engage with fibrous capsule FC. Catheter 312 may then be activated such that a direct or alternating current is passed through the resistant metal wire electrode of catheter 312 to generate heat at electrode tip 314, so that electrode tip 314 dissects fibrous capsule FC to form a puncture therein as illustrated in FIG. 5D. The puncture created in fibrous capsule FC may have a desired size to relieve a predetermined amount of pressure within kidney K. As will be understood by a person having ordinary skill in the art, the puncture may have various shapes, including, e.g., circular apertures or vertical or horizontal lacerations. Catheter 308 and/or catheter 312 may then be removed leaving guidewire 302 in place across the puncture. In accordance with another aspect of the present invention, when catheter 312 is used, catheter 312 may itself be used as the guidewire.

Figures 5E, 5F:
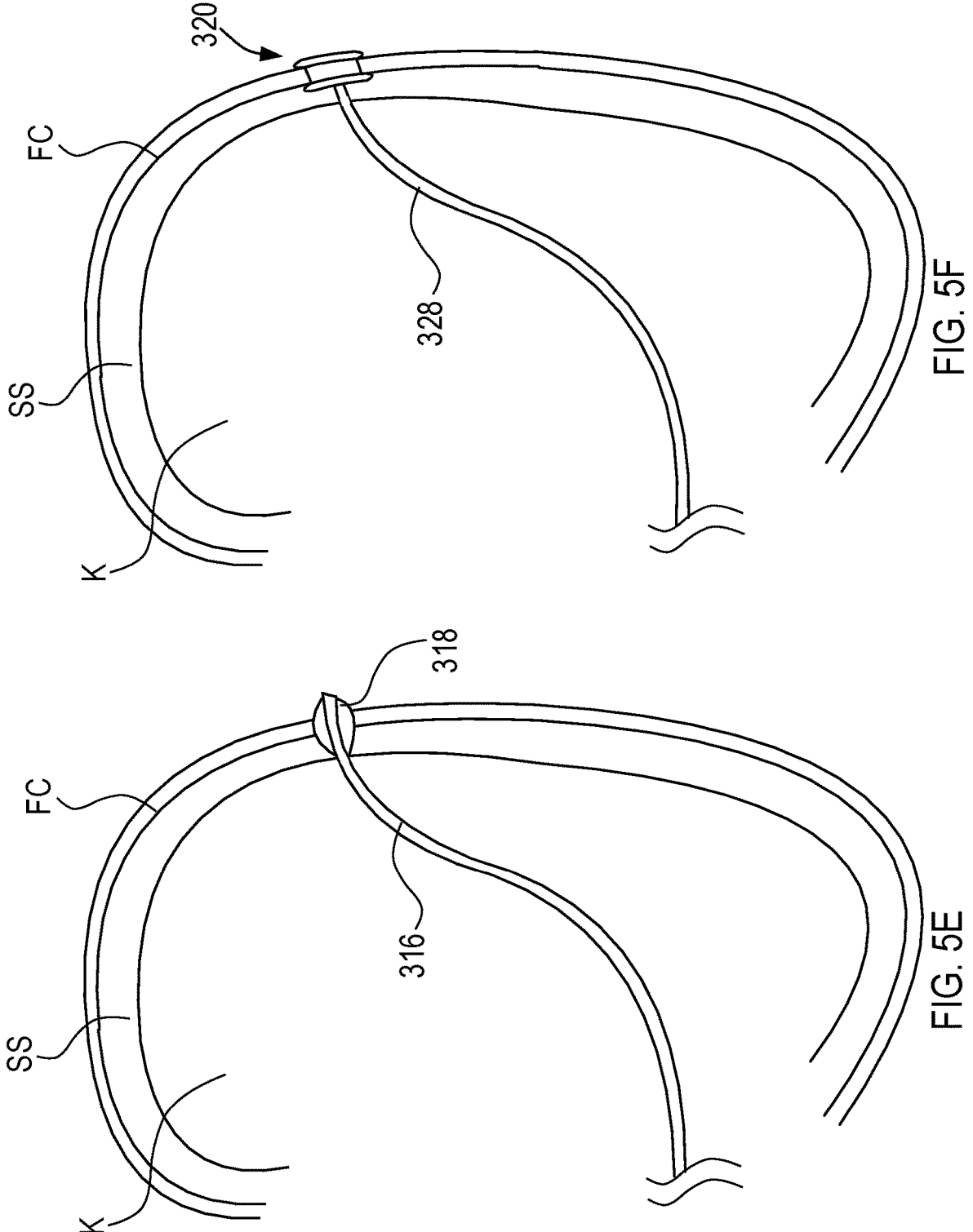

At step 404, the distal region of dilation catheter 316 is advanced to subcapsular space SS via guidewire 302 and positioned within the puncture of fibrous capsule FC created by the selected catheter in a deflated delivery state. In accordance with one aspect of the present invention, an introductory sheath may be disposed over dilation catheter 316, such that retraction of the sheath exposes expanded member 318. Expandable member 318 is then expanded to an inflated dilation state such that expandable member 318 dilates the puncture to a larger desired size as illustrated in FIG. 5E. For example, dilation catheter 316 may be actuated by delivering a fluid through a fluid lumen of dilation catheter 316 and into expandable member 318 via a fluid port disposed within expandable member 318 in fluid communication with the fluid lumen of dilation catheter 316. Expandable member 318 may then be deflated, e.g., by removing the fluid therein, such that expandable member 318 transitions from the inflated dilation state to the deflated delivery state, and removed from the patient. As will be understood by a person having ordinary skill in the art, dilation catheter 316 may be integrated with catheter 308 and/or catheter 312, such that expandable member 318 is disposed on the distal end of catheter 308 and/or catheter 312, thus requiring less delivery steps and components.

At step 406, spacer device 320 is advanced via guidewire 302 in a collapsed delivery state until spacer device 320 is positioned within the dilated puncture of fibrous capsule FC. Spacer device 320 is then transitioned from the collapsed delivery state to an expanded deployed state within the dilated puncture such that proximal end 322 of spacer device 320 is engages fibrous capsule FC from outside fibrous capsule FC, and distal end 324 of spacer device 320 engages fibrous capsule FC from within subcapsular space SS to anchor spacer device 320 within the dilated puncture as illustrated in FIG. 5F. For example, spacer device 320 may be delivered to the dilated puncture while coupled to delivery catheter 328 and/or within an introduction sheath.

Figure 5G:
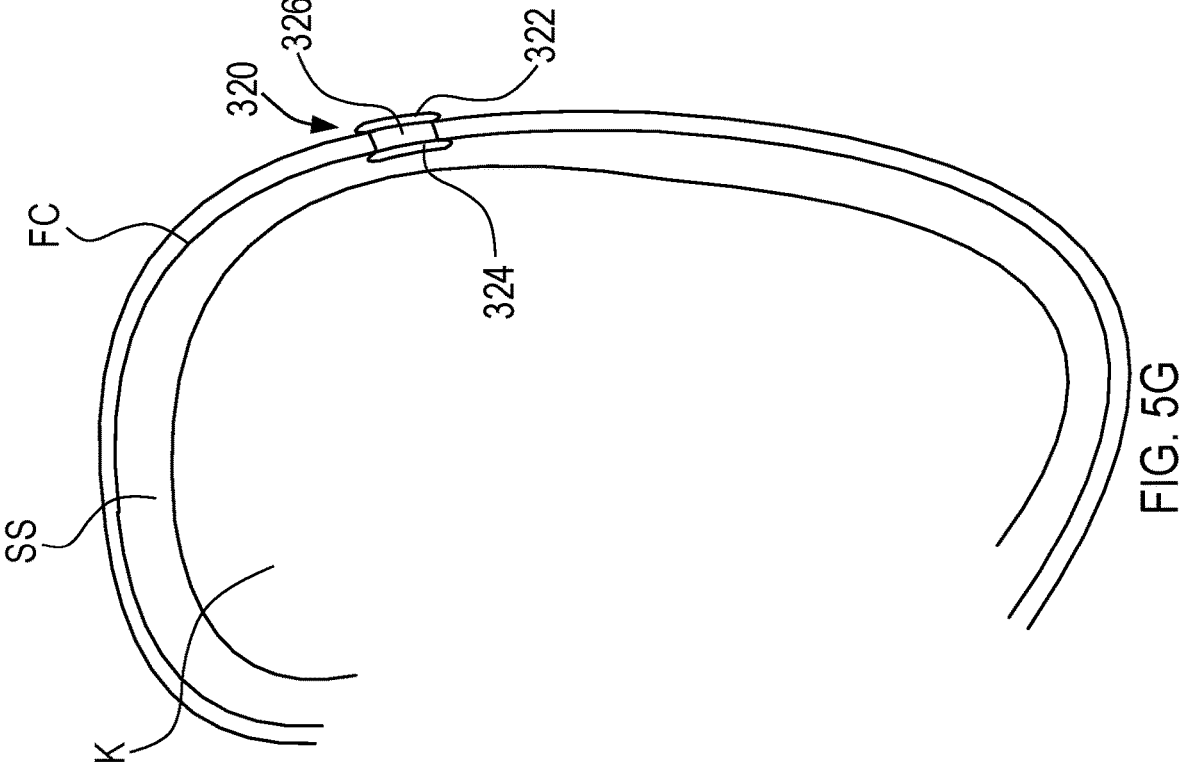

Accordingly, when spacer device 320 is properly positioned within the dilated puncture within the sheath, the sheath may be pulled back while spacer device 320 remains in position within the dilated puncture via delivery catheter 328 until spacer device 320 is exposed from the sheath and expands (e.g., self-expands, balloon expands) to the expanded deployed state. Delivery catheter 328 may then be decoupled from spacer device 320 and removed from the patient along with guidewire 302 as illustrated in FIG. 5G. In the expanded deployed state, intra-parenchymal pressure of kidney K is relieved through central opening 326 of spacer device 320 into a retroperitoneal cavity of the patient.

Spacer device 320 may include a one-way valve disposed within central opening 326 to regulate the pressure relief through spacer device 320 by permitting fluid to flow only from subcapsular space SS across fibrous capsule FC into the retroperitoneal cavity. For example, the valve may permit fluid to flow therethrough when a predetermined pressure gradient exists across the valve between subcapsular space SS and the space outside fibrous capsule FC. As will be understood by a person having ordinary skill in the art, method 400 may be repeated multiple times to create multiple punctures within the fibrous capsule of the renal capsule and deploy multiple spacer devices in the respective punctures to relieved a desired amount of pressure within the kidney.

As described above, with access to the subcapsular space of the renal capsule, numerous diagnostic and/therapeutic procedures may be performed such as measuring physiological parameters, e.g., build-up of renal pressure within the kidney and/or accumulating biomarkers of renal function/injury. For example, a system may be used to measure renal pressure.

Figure 6:
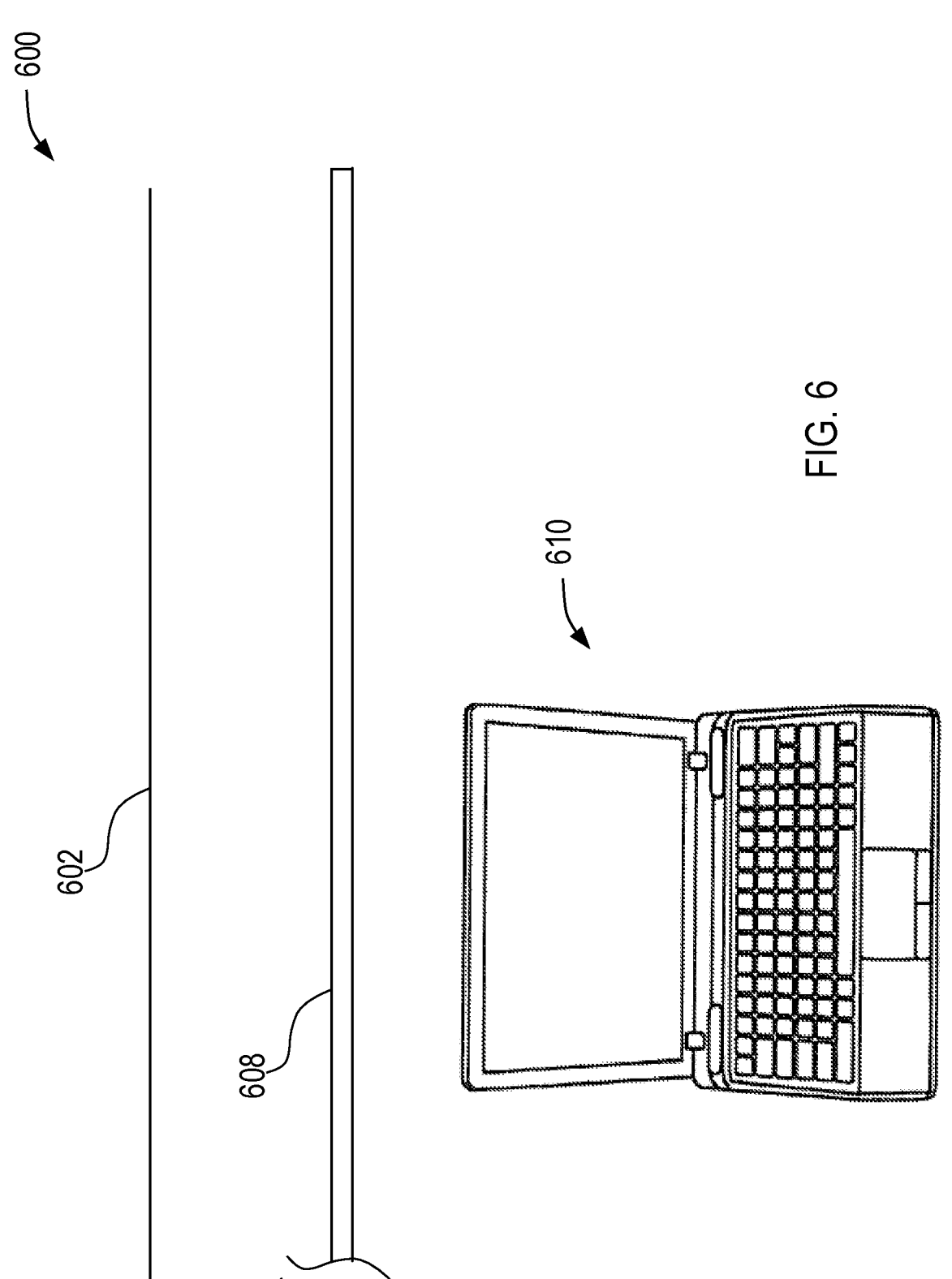
FIG. 6 illustrates an exemplary system for measuring a physiological parameter within a kidney of a patient in accordance with the principles of the present invention.

Referring now to FIG. 6, a system for measuring a physiological parameter, e.g., renal pressure or metabolite level, of a patient's kidney in accordance with the principles of the present invention is provided. System 600 includes guidewire 602, sensor catheter 608, and external computer 610. Guidewire 602 is constructed similar to guidewire 302 of FIG. 3. Sensor catheter 608 has sensing components designed to sense one or more physiological parameters. For example, sensor catheter 608 may be a sensor wire for measuring pressure within the subcapsular space of the renal capsule. Alternatively, or in addition to, sensor catheter 608 may be a catheter having sensor components disposed on the distal end thereof for measuring other physiological parameters. In accordance with another aspect of the present invention, sensor catheter 608 may be used to deliver the sensor components within the subcapsular space, e.g., a sensor chip, such that upon removal of sensor catheter 608, the sensor chip remains disposed within the subcapsular space and may communicate wirelessly with external computer 610.

Sensor catheter 608 and/or its sensor components (collectively the "sensors") are further designed to generate a signal indicative of the measured renal pressure. For example, the sensors are operatively coupled to external computer 610, e.g., via a wired or wireless communication, such that the sensors may transmit and external computer 610 may receive the generated signal indicative of the measured renal pressure. External computer 610 further may include non-transitory computer readable media having instructions that, when executed by a processor of external computer 610, cause the processor to compare the measured renal pressure based on the signal with a threshold renal pressure stored in a memory of the processor, and causes external computer 610 to generate an alert if the measured renal pressure is above the threshold renal pressure. Accordingly, the surgeon will be informed of when the patient's renal pressure needs to be decreased. Alternatively, or additionally, the generated signal indicative of the measured renal pressure may be used as part of a closed-loop feedback system.

In accordance with another aspect of the present invention, the sensors may be designed to transmit the signal indicative of the measured physiological parameter to an assist device implanted or otherwise coupled to the patient for impacting kidney blood flow, e.g., a ventricular assist device, a mechanical circulatory support such as a dialysis machine.

Figure 7A:
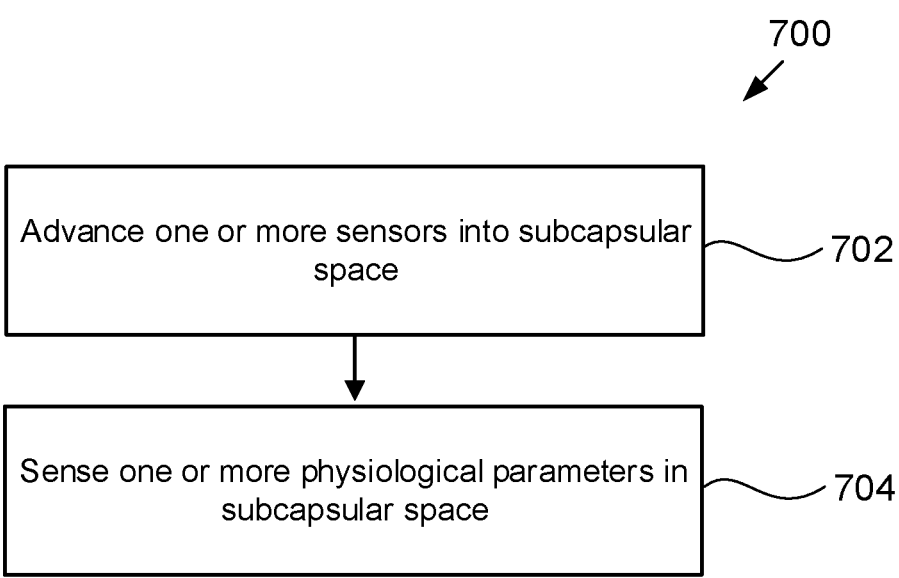
FIG. 7A is a flow chart of steps in an exemplary method for measuring physiological parameters within a kidney of a patient in accordance with the principles of the present invention.

Referring now to FIG. 7A, an exemplary method for performing a diagnostic procedure (step 106 of FIG. 1) is provided. Specifically, method 700 for measuring physiological parameters within a patient's kidney using system 600 is provided. At step 702, one or more sensors are advanced into subcapsular space SS. For example, the sensors may be disposed on a distal region of sensor catheter 608, and thus delivered along with sensor catheter 608 via guidewire 602 and positioned within subcapsular space SS as illustrated in FIG. 8. In accordance with another aspect of the present invention, the sensor may be a wire-based sensor that is delivered within the subcapsular space through the lumen of the micro-catheter. Alternatively, sensor catheter 608 may be used to deliver sensing components, e.g., pressure sensors such as a sensor chip, to the subcapsular space, and may subsequently be removed, leaving the sensor chip disposed within the subcapsular space. Accordingly, the sensors may be implanted within the subcapsular space of the renal capsule for prolonged diagnostics. At step 704, the one or more sensors may sense one or more physiological parameters within subcapsular space SS of the patient's renal capsule. For example, the sensors may sense renal pressure within the subcapsular space as described in further detail below with reference to FIG. 7B.

Moreover, the sensed physiological parameters may be transmitted to an assist device implanted in or otherwise coupled to the patient designed to impact blood flow within the patient's kidney. Additionally, or alternatively, a feedback signal may be generated based on the sensed physiological parameters.

Figure 7B:
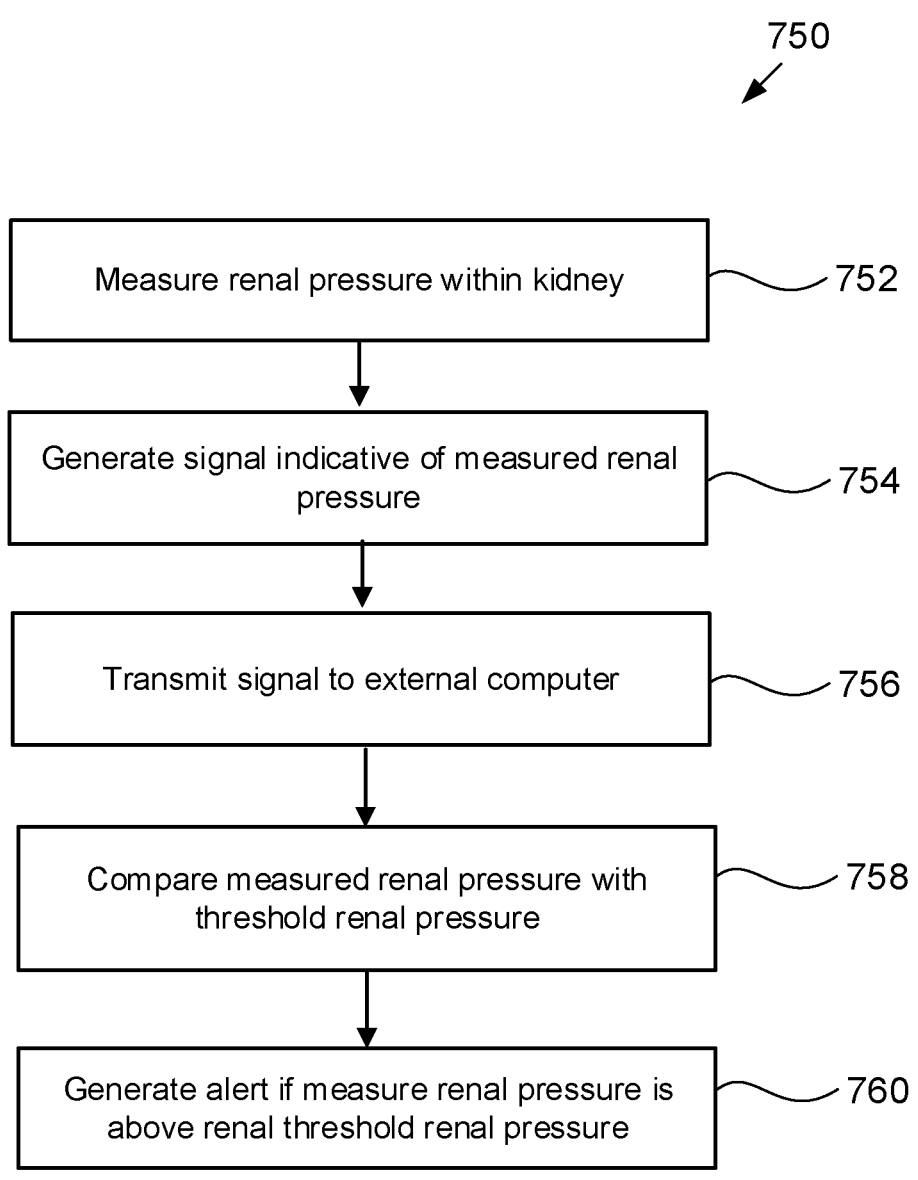
FIG. 7B is a flow chart of steps in an exemplary method for measuring a physiological parameter within a kidney of a patient in accordance with the principles of the present invention.
Figure 8:
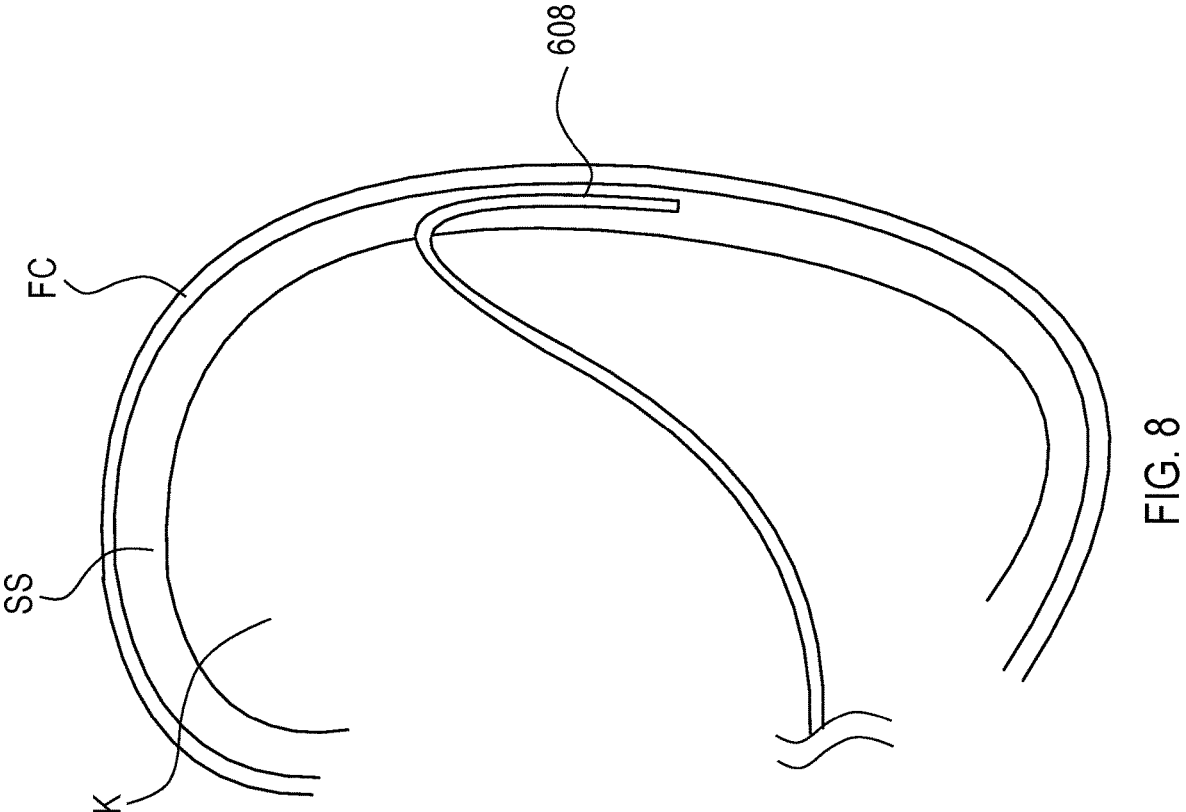
FIG. 8 illustrates steps taken during the method of FIG. 7A, according to some embodiments of the present invention.

Referring now to FIG. 7B, method 750 for measuring physiological parameter, e.g., renal pressure, of a patient's kidney using system 600 is provided. At step 752, sensor catheter 608 measures the pressure within subcapsular space SS of the patient's renal capsule. At step 754, sensor catheter 608 generates a signal indicative of the measured renal pressure, and at step 756, sensor catheter 608 transmits the signal to external computer 610, e.g., either wirelessly or via electrical cable(s) coupled to sensor catheter 408 and external computer 610.

At step 758, the instructions of the non-transitory computer readable media of external computer 610 are executed by the processor of external computer 610 cause the processor to compare the measured renal pressure based on the signal received from sensor catheter 608 with a threshold renal pressure stored in a memory of the processor to determine whether the measure renal pressure is above the threshold renal pressure. If the measured renal pressure is above the threshold renal pressure, external computer 610 generates an alert, e.g., audible or visible alarm, at step 760 to alert the physician. Accordingly, the physician will be informed when the patient's renal pressure is too high and needs to be decreased, and thus will be able to take the necessary steps to reduce the renal pressure of the patient's kidney. Sensor catheter 608 and/or the sensing components may remain within the renal capsule of the patient for a desired amount of time, and may be removed from the patient upon completion of the procedure.

Figures 9A, 9B:
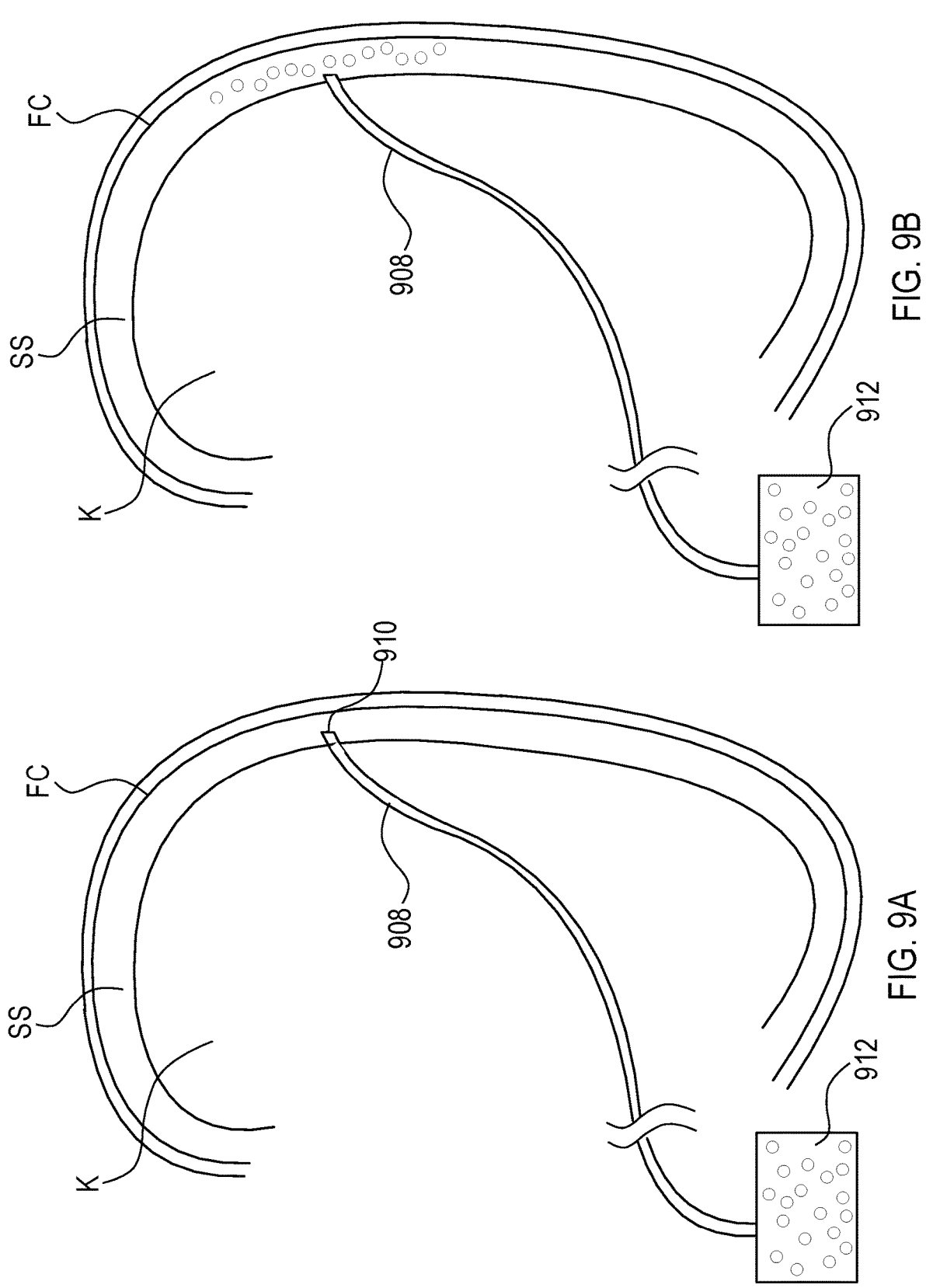
FIGS. 9A-9B illustrate an exemplary method for delivering drug therapy to a kidney of a patient in accordance with the principles of the present invention.

As described above, with access to the subcapsular space of the renal capsule, numerous diagnostic and/therapeutic procedures may be performed such as delivering drug therapy to the renal capsule. For example, as shown in FIG. 9A, the distal region of drug-eluting catheter 908 is advanced via a guidewire until outlet 910 is positioned in the desired position within subcapsular space SS of the renal capsule. The guidewire may then be removed. Subsequently, the proximal region of drug-eluting catheter 908 may be coupled to reservoir 912 if not already coupled prior to removal of the guidewire. Reservoir 912 is sized and shaped to store a sufficient amount of the renal drug required for the drug therapy. For example, the renal drug may be a drug that reduces kidney fibrosis, enhances fluid removal with diuretics, or treats localized diseases such as kidney cancer, or any combination thereof. Additionally, reservoir 912 includes a pump for delivering the renal drug from reservoir 912 through the lumen of drug-eluting catheter 908.

The renal drug may then be delivered from reservoir 912 through the drug-delivery lumen of drug-eluting catheter 908 and outlet 910 within subcapsular space SS as illustrated in FIG. 9B. Drug-eluting catheter 908 may be removed from the patient upon completion of the drug delivery procedure.

Additionally, or alternatively, the distal region of drug-eluting catheter 908 may be a drug-eluting balloon designed to deliver drug therapy upon expansion of the balloon. For example, the drug-eluting balloon may be coated with the drug such that upon expansion, the drug contacts surrounding tissue and/or fluid within the subcapsular space to release the drug, or the drug-eluting balloon may be porous such that a drug is delivered to the balloon to expand the balloon and flows across the pores into the subcapsular space. By delivering the drug directly to the subcapsular space of the renal capsule, e.g., localized delivery, wash away of the drug is reduced as the drug is not introduced into systemic circulation.

As described above, with access to the subcapsular space of the renal capsule, numerous diagnostic and/therapeutic procedures may be performed such as displacing the fibrous capsule from the kidney to accommodate changes in renal pressure. For example, a system may be used to position an inflatable flat-winged balloon within the subcapsular space, and inflate the balloon to stretch the fibrous capsule and/or dissect the fibrous capsule off of the kidney, thereby expanding the subcapsular space so the renal capsule may accommodate changes in renal volume without necessarily perforating or disrupting capsule integrity.

Figure 10:
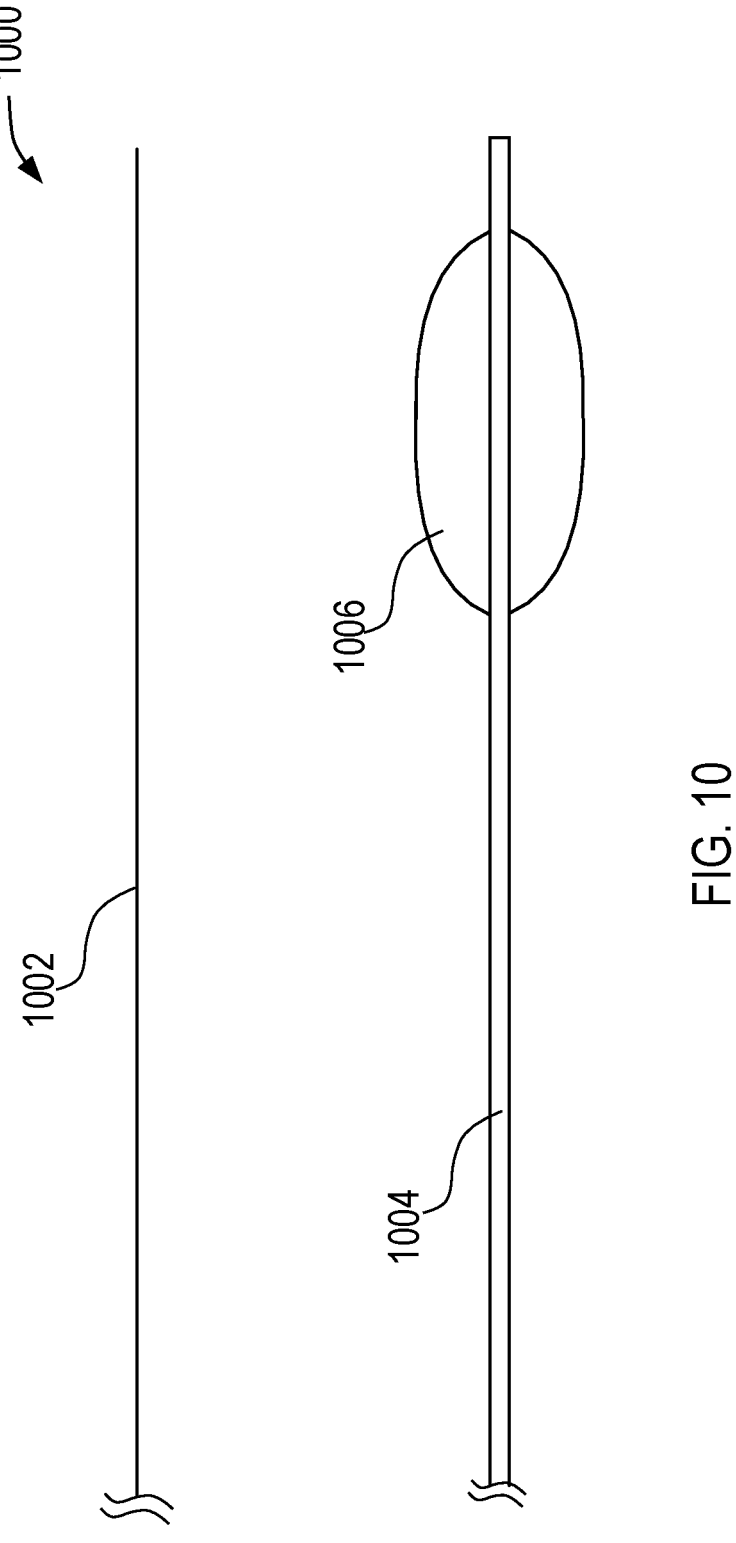
FIG. 10 illustrates an exemplary system for displacing a fibrous capsule from a kidney of a patient in accordance with the principles of the present invention.

Referring now to FIG. 10, a system for displacing the fibrous capsule from the kidney in accordance with the principles of the present invention is provided. System 1000 includes guidewire 1002, and balloon catheter 1004 having expandable member 1006 disposed at the distal end thereof. Guidewire 1002 is constructed similar to guidewire 302 of FIG. 3. Expandable member 1006 may be, e.g., an inflatable balloon. For example, balloon 1006 may be a flat-winged balloon having a flat configuration in a collapsed state and an expanded configuration in an inflated state. Accordingly, balloon 1006 may be delivered to the subcapsular space over guidewire 1002 within an introductory sheath, e.g., intra-vascularly or non-vascularly. In addition, the interior of balloon 1006 may be in fluid communication with a source of fluid external to the patient's body via a fluid lumen of catheter 1004 for inflation and deflation of balloon 1006. In the inflated state, balloon 1006 is sized and shaped to displace the fibrous capsule from the kidney to stretch the fibrous capsule and/or dissect the fibrous capsule from the kidney without perforating or disrupting capsule integrity. As will be understood by a person having ordinary skill in the art, other expandable devices may be used to displace the fibrous capsule from the kidney.

Figure 11:
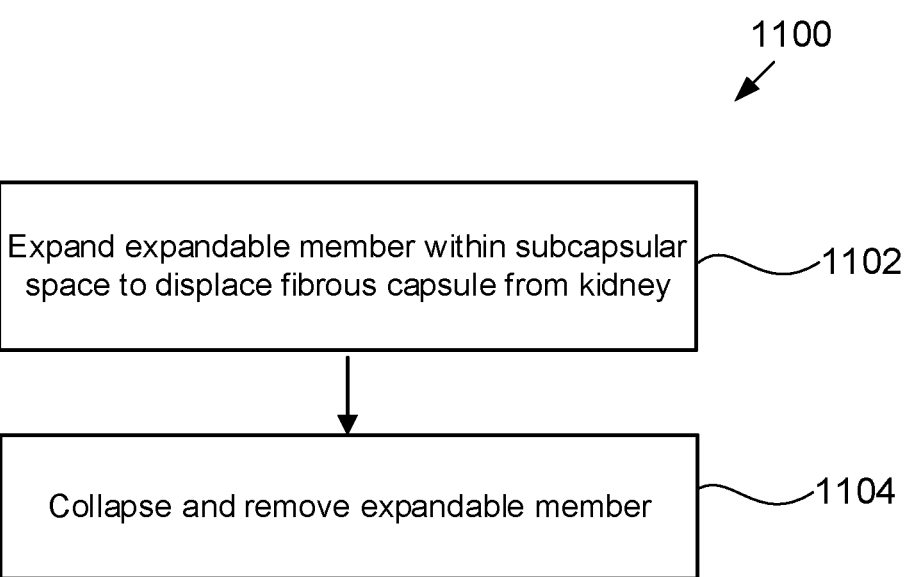
FIG. 11 is a flow chart of steps in an exemplary method for displacing a fibrous capsule from a kidney of a patient in accordance with the principles of the present invention.
Figures 12A, 12B:
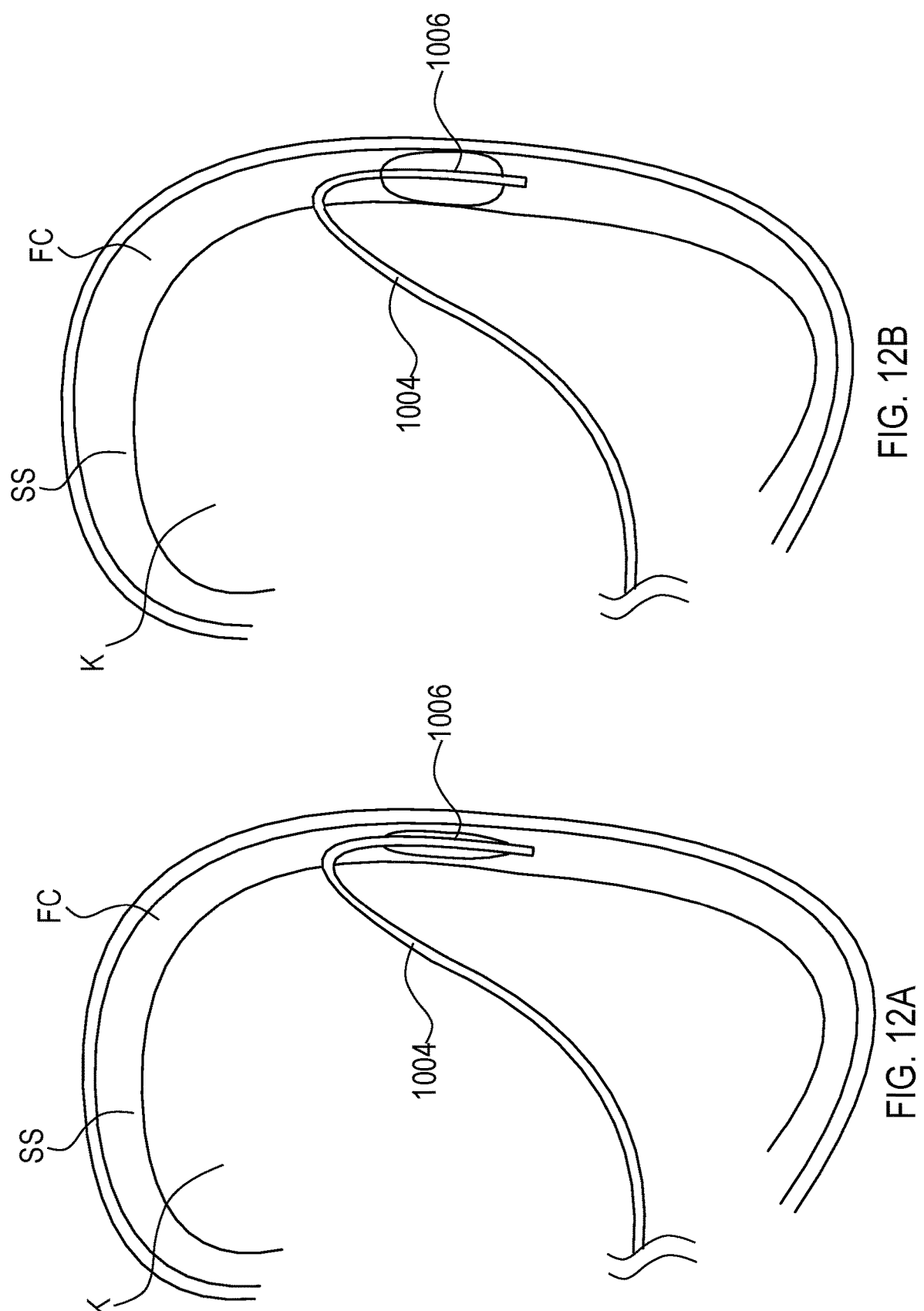
FIGS. 12A-12C illustrate steps taken during the method of FIG. 11, according to some embodiments of the present invention.

Referring now to FIG. 11, an exemplary method for performing a therapeutic procedure (step 106 of FIG. 1) is provided. Specifically, method 1100 for displacing the fibrous capsule from the kidney using system 1000 is provided. Some of the steps of method 1100 may be further elaborated by referring to FIGS. 12A-12C. As illustrated in FIG. 12A, balloon catheter 1004 having balloon 1006 disposed thereon is advanced to subcapsular space SS, as described above with respect to step 104 of FIG. 1. As further shown in FIG. 12A, balloon 1006 is initially in a deflated, collapsed state.

Figure 12C:
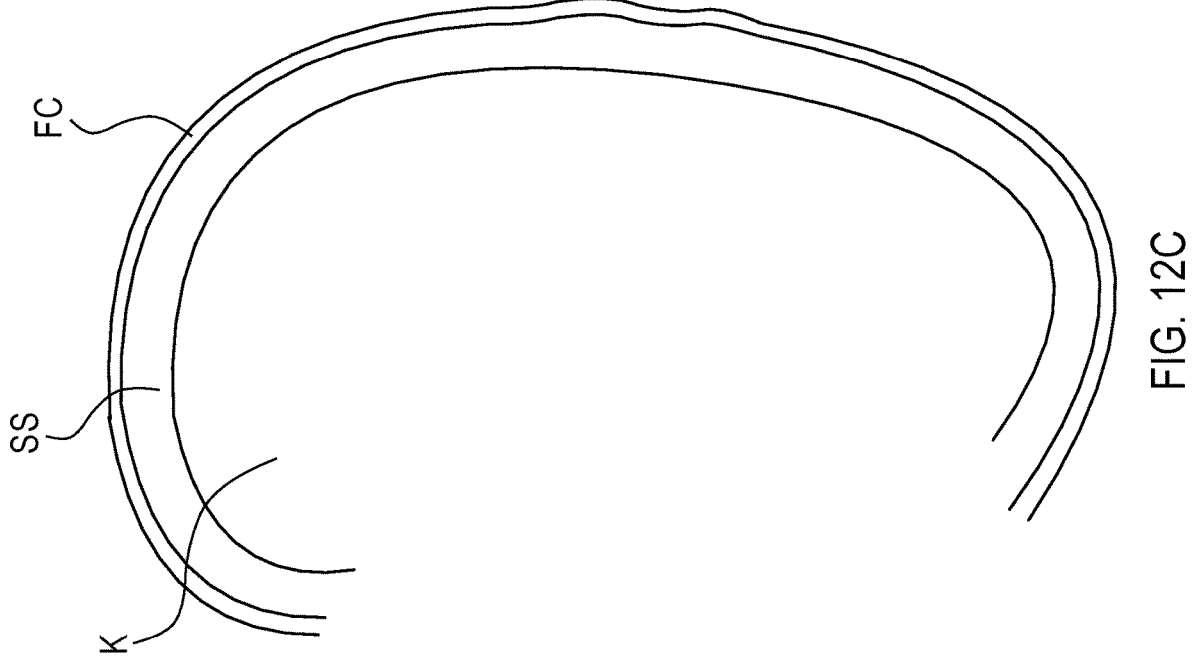

At step 1102, the expandable member, e.g., balloon 1006, is inflated to an expanded state within subcapsular space SS as shown in FIG. 12B. Inflation of balloon 1006 will apply force to displace fibrous capsule FC from kidney K, thereby stretching fibrous capsule FC and/or dissecting fibrous capsule FC from kidney K. At step 1104, balloon 1006 is deflated and removed from the patient as shown in FIG. 12C. Upon removal of balloon 1006 from the subcapsular space, the stretched fibrous capsule FC will be able to better accommodate changes in renal volume.

In accordance with another aspect of the present invention, the catheter advanced within the subcapsular space may have an inlet disposed at its distal end, and its proximal end may be coupled to a mechanism for directly removing fluid from within the subcapsular space through the lumen of the catheter for collection outside the patient's body to directly reduce renal pressure. For example, the mechanism may include a pump, siphon, pressure valve, or other any other mechanisms readily known in the art.

Figure 13B:
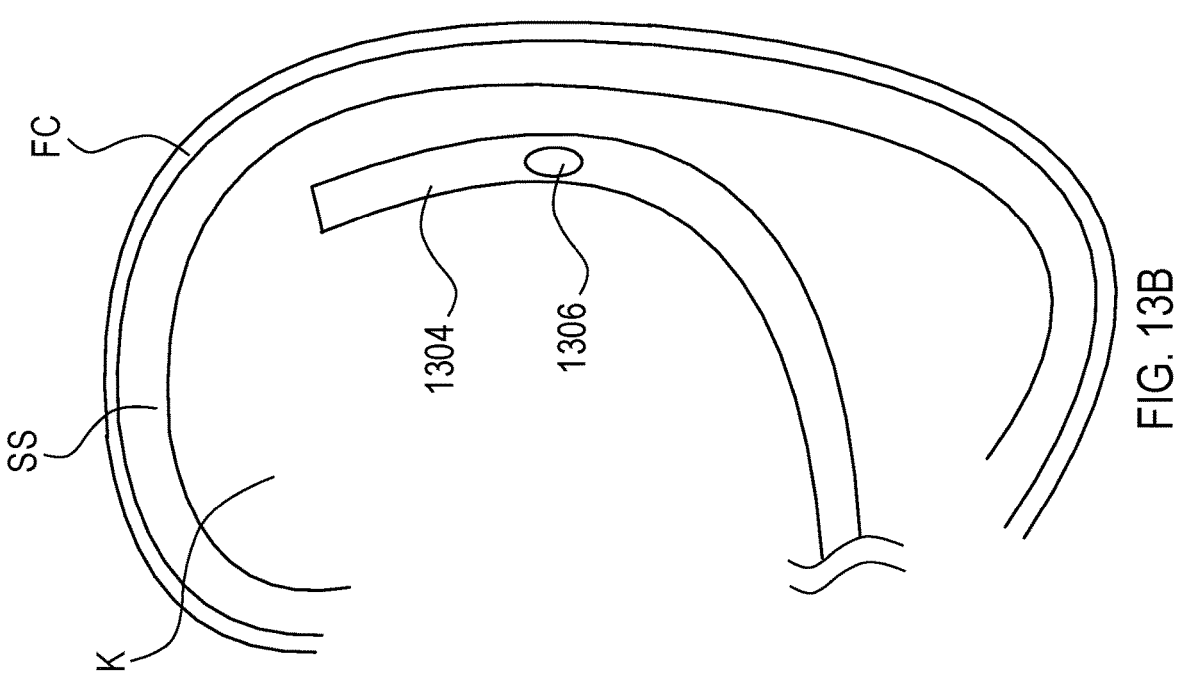
FIGS. 13A-13C illustrate an alternative system for accessing the subcapsular space of a patient's renal capsule in accordance with the principles of the present invention.
Figure 13A:
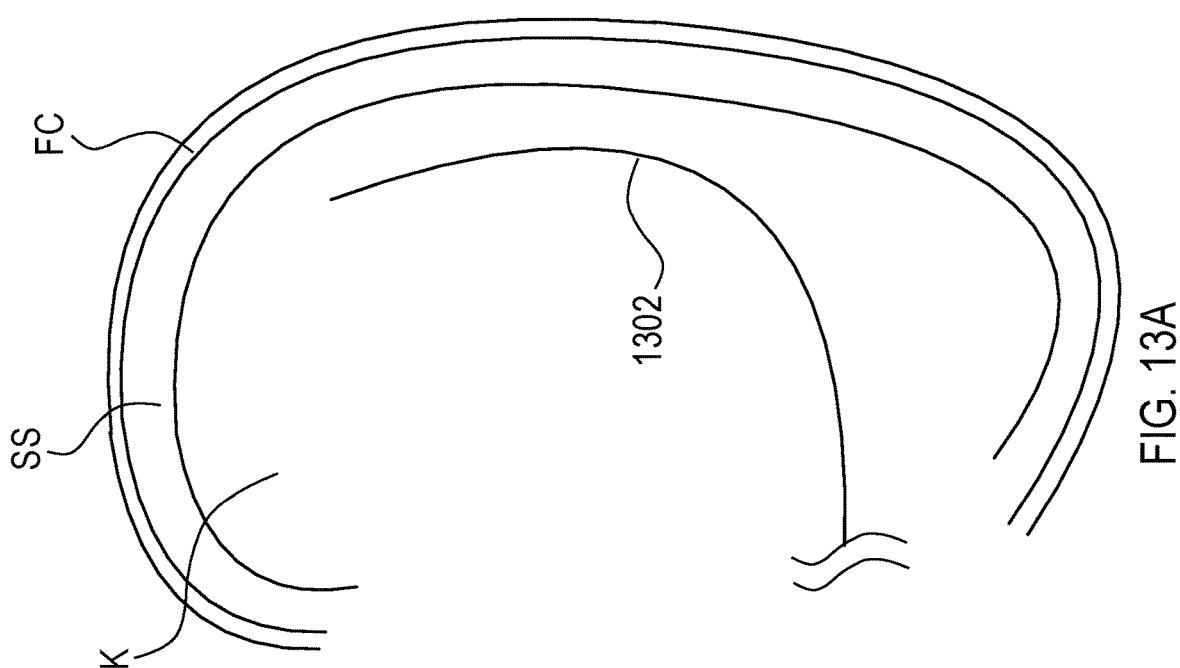
Figure 13C:
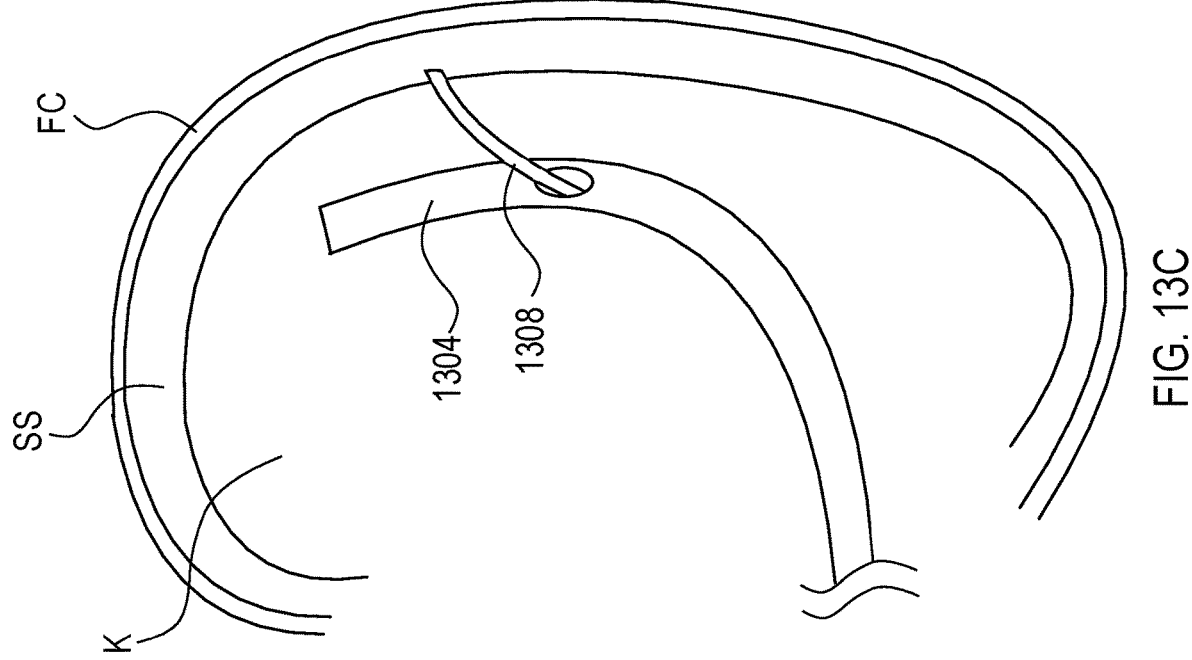

In accordance with another aspect of the present invention, catheter 1304 having side port 1306 may be used to deliver the micro-catheter to the subcapsular space of the renal capsule. For example, as shown in FIG. 13A, guidewire 1302 may first be advanced to a position adjacent to subcapsular space SS surrounding kidney K from within kidney K. As shown in FIG. 13B, the distal region of catheter 1304 is advanced via guidewire 1302 until it is positioned adjacent to subcapsular space SS surrounding kidney K. Guidewire 1302 may then be removed. Further, as shown in FIG. 13C, micro-catheter 1308 is advanced through the lumen of first catheter 1304 and out of catheter 1304 via side port 1306, such that the distal end of micro-catheter 1308 enters and is positioned within subcapsular space SS. As described above, with access to the subcapsular space of the renal capsule, numerous diagnostic and/or therapeutic procedures may be performed.

Referring now to FIGS. 14A-14I, additional proof-of-concept of the principles of the present invention is provided. Specifically, pilot studies were conducted to illustrate the ability to place wires and catheters in the subcapsular space with dependable reproducibility and speed of the procedure, e.g., 10-15 minutes. In addition, the studies illustrate the ability to remove fluid from the subscapular space, and to deliver materials include sensors, balloons, wires, fluid, and dyes into the subcapsular space, as well as to disrupt the integrity of the renal capsule, i.e., decapsulation, using catheter based techniques in accordance with the principles of the present invention, without the need for surgery.

Figure 14A:
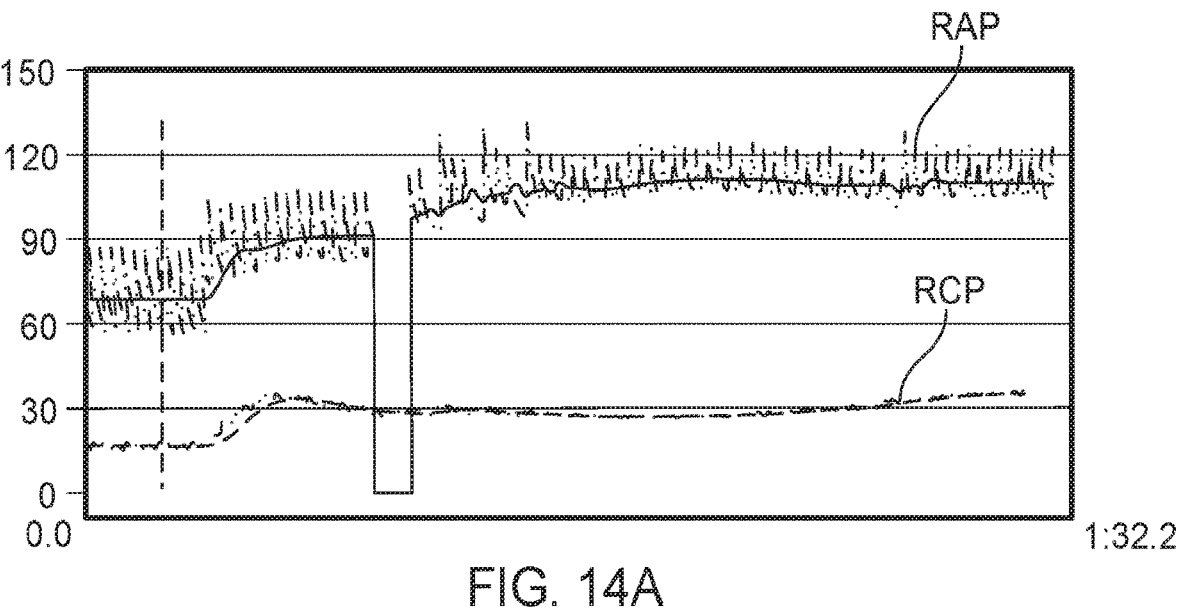
FIGS. 14A-14I illustrate additional proof-of-concept of the principles of the present invention.

For example, FIG. 14A illustrates the association between increasing renal arterial pressure RAP and renal capsular pressure RCP as may be seen with hypertension, renal arterial disease, or use of circulatory support pumps. The vertical line denotes the point of activation of an extracorporeal membrane oxygenation (ECMO) machine to increase the subject's renal arterial pressure. As shown in FIG. 14A, RAP overload increases RCP.

Figure 14B:
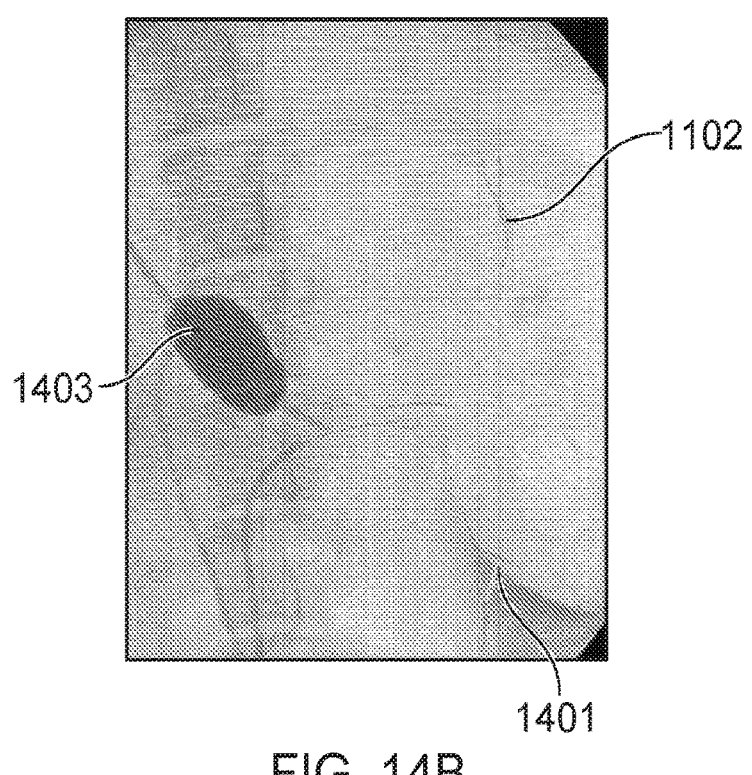
Figure 14C:
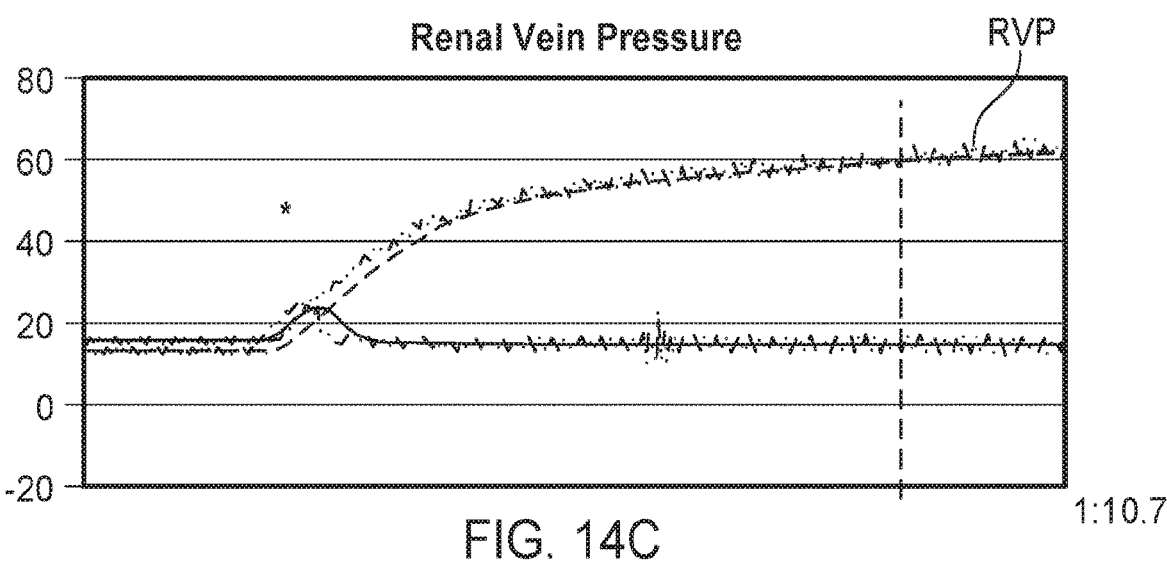
Figure 14D:
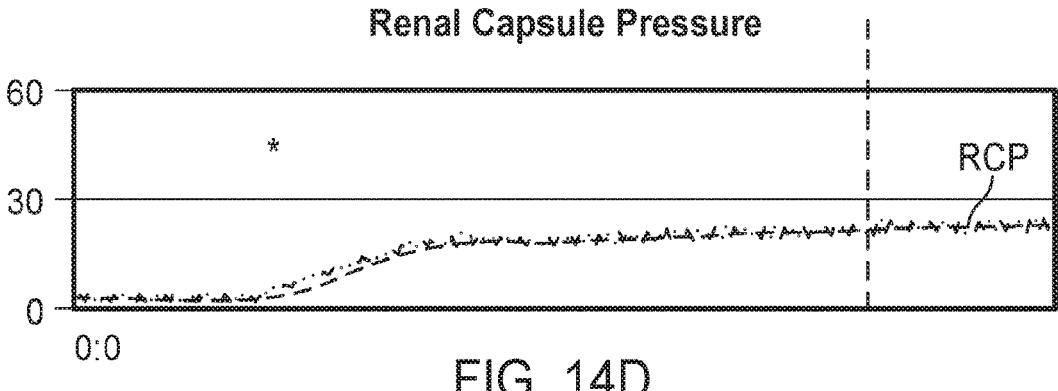
Figure 14E:
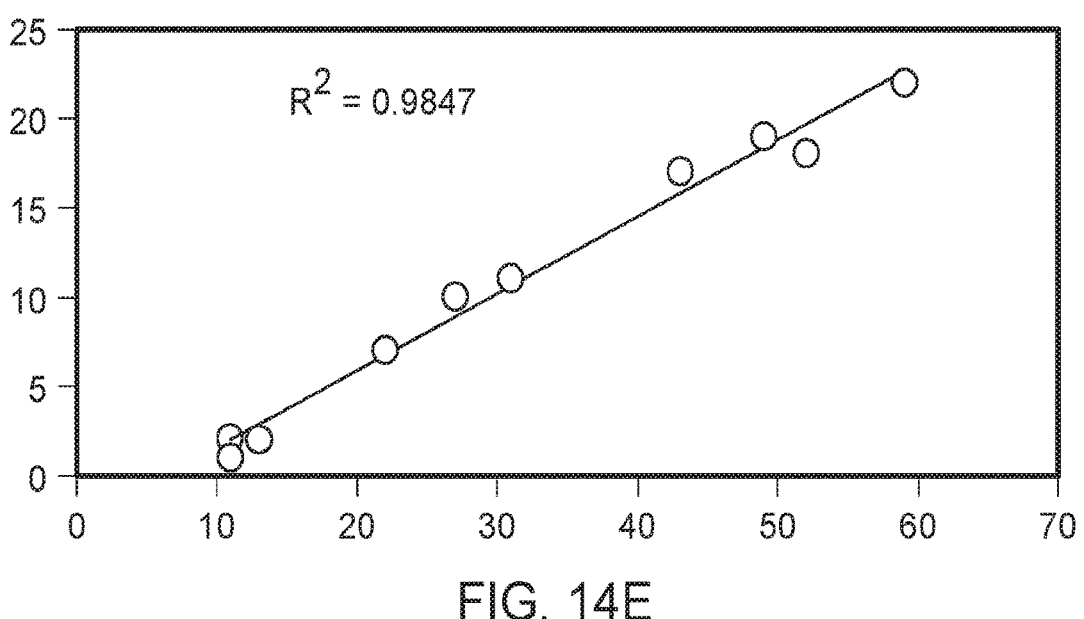

FIGS. 14B-14E illustrate the association between increasing renal vein pressure RVP and RCP as may be seen with heart failure, pulmonary hypertension, liver failure, clot in the vena cava, abdominal pressure overload, kidney failure, or any condition with increased systemic venous pressure or volume overload. For example, FIG. 14B illustrates sensor wire 1401 disposed within subcapsular space SS, pressure sensor 1402 disposed within renal vein RV, and balloon 1403 disposed in an inflated state within renal vein RV. The inflation of balloon 1403 causes occlusion of renal vein RV, thereby increasing RVP as shown in FIG. 14C, and accordingly increasing RCP as shown in FIG. 14D. As shown in FIGS. 14C-14E, RVP overload increases RCP.

Figure 14F:
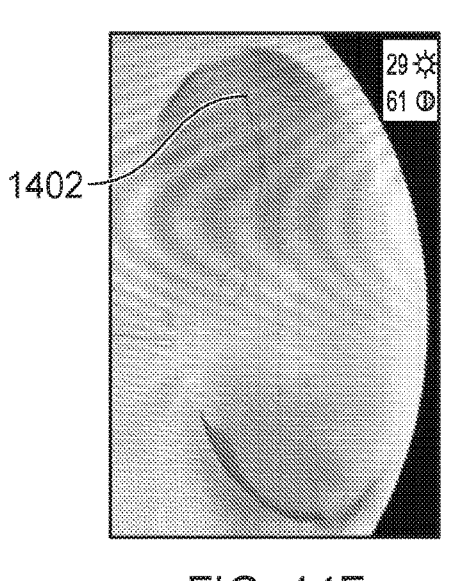
Figure 14H:
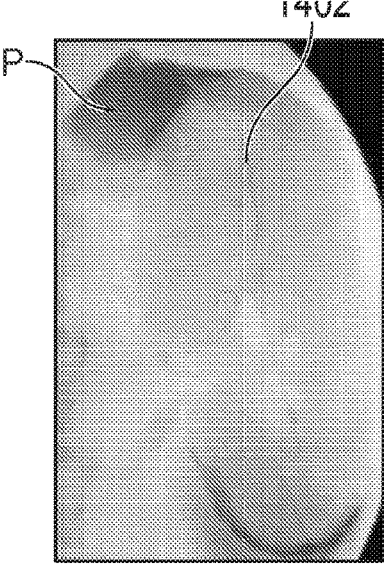
Figure 14G:
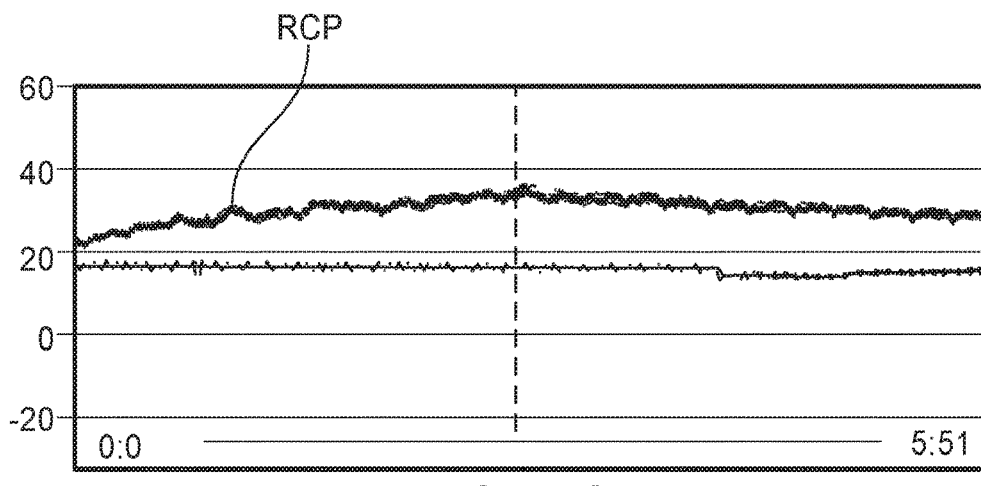
Figure 14I:
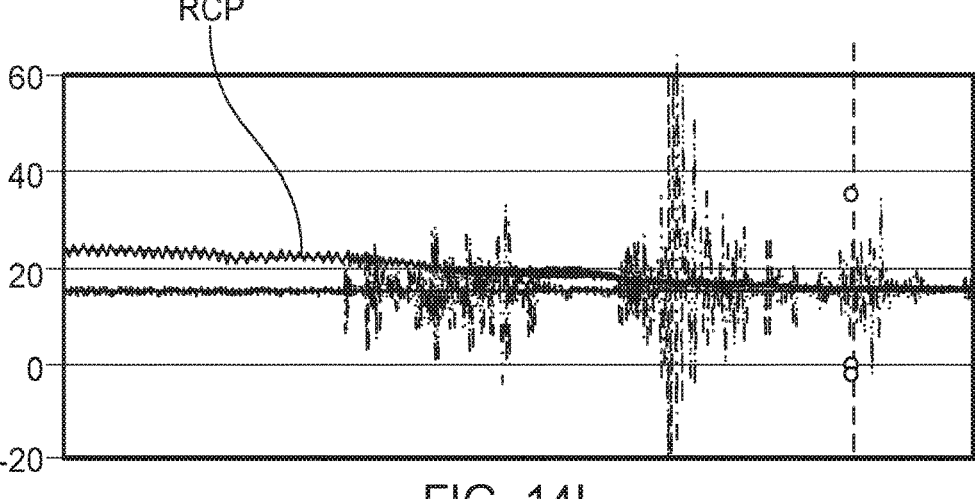

FIGS. 14F-14I illustrate the association between decapsulation of the renal capsule and reduced RVP in the setting of renal tamponade, i.e., increasing renal capsule volume/pressure. For example, FIG. 14F illustrates the injection of a fluid, e.g., saline and contrast dye, into subcapsular space SS, thereby increasing RCP as shown in FIG. 14G. Specifically, FIG. 14G illustrates that increasing renal tamponade increases RVP and decreases renal arterial flow. The vertical line denotes the point of decapsulation of the renal capsule. FIG. 14H illustrates perforation P of the renal capsule. As further shown in FIGS. 14G and 14I, after decapsulation of the renal capsule, RCP decreases, and accordingly RVP is also reduced.

While various illustrative embodiments of the invention are described above, it will be apparent to one skilled in the art that various changes and modifications may be made herein without departing from the invention. It will further be appreciated that the systems and methods described herein may be utilized for decapsulation of organs other than the kidney or the heart. The appended claims are intended to cover all such changes and modifications that fall within the true spirit and scope of the invention.

What is claimed:

1. A method for accessing a subcapsular space of a renal capsule of a patient's kidney, the method comprising:
   advancing a guidewire to a position within the subcapsular space of the renal capsule of the patient's kidney from within the patient's kidney;
   advancing a distal end of a micro-catheter via the guidewire such that the distal end of the micro-catheter is disposed within the subcapsular space of the renal capsule; and
   performing a diagnostic or therapeutic procedure, or both, within the subcapsular space using the micro-catheter.

2. The method of claim 1, further comprising using electrocautery to form a puncture in a fibrous capsule surrounding the subcapsular space of the renal capsule.

3. The method of claim 2, wherein the micro-catheter comprises a wire having the electrocautery.

4. The method of claim 1, wherein performing the diagnostic or therapeutic procedure, or both, within the subcapsular space comprises using a sensor disposed in the subcapsular space via the micro-catheter to measure a physiological parameter and to generate a signal indicative of the measured physiological parameter.

5. The method of claim 1, wherein advancing the guidewire to the position within the subcapsular space of the renal capsule of the patient's kidney comprises advancing the guidewire intravascularly via at least one of arterial, venous, or lymphatic vessels.

6. The method of claim 1, wherein advancing the guidewire to the position within the subcapsular space of the renal capsule of the patient's kidney comprises advancing the guidewire non-vascularly via a ureter of the patient.

7. The method of claim 1, wherein advancing the guidewire to the position within the subcapsular space of the renal capsule of the patient's kidney comprises advancing the guidewire transcutaneously.

8. The method of claim 1, wherein performing the diagnostic or therapeutic procedure, or both, within the subcapsular space comprises performing the therapeutic procedure to reduce intra-renal pressures to treat heart failure.

9. The method of claim 1, wherein performing the diagnostic or therapeutic procedure, or both, within the subcapsular space comprises decapsulating.

10. The method of claim 1, wherein performing the diagnostic or therapeutic procedure, or both, within the subcapsular space comprises performing the diagnostic procedure to monitor intra-renal pressures for heart failure.

11. The method of claim 1, wherein the distal end of the micro-catheter is further configured to form a puncture in a fibrous capsule surrounding the subcapsular space of the renal capsule, the method further comprising:

puncturing the fibrous capsule via the distal end of the micro-catheter to form the puncture in the fibrous capsule;

delivering a dilation catheter having an expandable member disposed thereon to the puncture of the fibrous capsule;

actuating the expandable member within the puncture to dilate the puncture of the fibrous capsule to a dilated size; and anchoring a spacer device within the puncture of the fibrous capsule to maintain the dilated size of the puncture.

12. The method of claim 11, wherein maintaining the dilated size of the puncture relieves intra-parenchymal pressure within the kidney, thereby improving renal function.

13. The method of claim 11, wherein the expandable member comprises a balloon, and wherein actuating the expandable member within the puncture to dilate the puncture of the fibrous capsule to the dilated size comprises expanding the balloon within the puncture of the fibrous capsule.

14. The method of claim 11, wherein the spacer device comprises a one-way valve.

15. The method of claim 11, wherein the micro-catheter comprises a wire having an electrocautery, such that puncturing the fibrous capsule comprises dissecting the fibrous capsule via the electrocautery of the wire to form the puncture in the fibrous capsule.

16. The method of claim 11, further comprising:

disposing a sensor in the subcapsular space via the micro-catheter;

measuring a physiological parameter within the subcapsular space via the sensor; and generating a signal indicative of the measured physiological parameter.

17. The method of claim 16, further comprising receiving the signal indicative of the measure physiological parameter via an external computer operatively coupled to the sensor.

18. The method of claim 17, further comprising processing, via a processor of the external computer, the signal indicative of the measured physiological parameter.

19. The method of claim 18, further comprising using the processed signal in a closed-loop feedback system.

20. The method of claim 17, further comprising:

comparing the measured physiological parameter based on the signal with a threshold physiological parameter; and generating an alert if the measured physiological parameter is above the threshold physiological parameter.

21. The method of claim 17, further comprising generating a feedback signal based on the received signal indicative of the measure physiological parameter.

22. The method of claim 16, wherein the sensor comprises a sensor wire.

23. The method of claim 16, wherein the sensor is a chip.

24. The method of claim 16, further comprising receiving the signal indicative of the measure physiological parameter via an assist device configured to impact blood flow within the patient's kidney.

25. The method of claim 1, wherein performing the diagnostic or therapeutic procedure, or both, within the subcapsular space comprises using the micro-catheter to deliver into the subcapsular space.

26. The method of claim 1, wherein performing the diagnostic or therapeutic procedure, or both, within the subcapsular space comprises relieving intra-renal pressure associated with hypertension.

27. The method of claim 1, further comprising delivering at least one of a drug, stem cells, viruses for gene therapy, RNAi, nanoparticles, or dyes into the subcapsular space of the renal capsule via the micro-catheter.

28. The method of claim 27, wherein the drug is configured to reduce kidney fibrosis, enhance fluid removal with diuretics, or treat localized diseases, or any combination thereof.

29. The method of claim 28, wherein the localized disease treated is cancer.

30. The method of claim 1, further comprising directly removing fluid from within the subcapsular space through the distal end of the micro-catheter and collecting the fluid outside the patient's body to directly reduce renal pressure.

31. The method of claim 1, further comprising:

expanding an expandable member disposed on the distal end of the micro-catheter to displace a fibrous capsule surrounding the kidney;

collapsing the expandable member; and removing the micro-catheter and expandable member from the subcapsular space.

32. The method of claim 31, wherein the expandable member comprises a balloon, and wherein expanding the expandable member comprises expanding the balloon to displace the fibrous capsule surrounding the kidney.

\* \* \* \* \*